(12) United States Patent
Joshi et al.

(10) Patent No.: US 10,111,838 B2
(45) Date of Patent: Oct. 30, 2018

(54) PHARMACEUTICAL OR NUTRACEUTICAL COMPOSITION WITH RESISTANCE AGAINST THE INFLUENCE OF ETHANOL

(71) Applicant: Evonik Roehm GmbH, Darmstadt (DE)

(72) Inventors: Shraddha Joshi, Navi Mumbai (IN); Ashish Guha, Dombivali (IN); Vinay Jain, Indore (IN)

(73) Assignee: Evonik Roehm GmbH, Darmstadt (DE)

( * ) Notice: Subject to any disclaimer, the term of this patent is extended or adjusted under 35 U.S.C. 154(b) by 0 days.

(21) Appl. No.: 15/518,429

(22) PCT Filed: Nov. 23, 2015

(86) PCT No.: PCT/EP2015/077302
§ 371 (c)(1),
(2) Date: Apr. 11, 2017

(87) PCT Pub. No.: WO2016/083278
PCT Pub. Date: Jun. 2, 2016

(65) Prior Publication Data
US 2017/0304211 A1    Oct. 26, 2017

(30) Foreign Application Priority Data

Nov. 26, 2014 (IN) ............................ 5930/CHE/2014

(51) Int. Cl.
| | |
|---|---|
| *A61K 9/50* | (2006.01) |
| *A61K 9/16* | (2006.01) |
| *A61K 9/28* | (2006.01) |
| *A61K 31/135* | (2006.01) |
| *A61K 31/138* | (2006.01) |
| *A61K 31/522* | (2006.01) |

(52) U.S. Cl.
CPC .......... *A61K 9/5026* (2013.01); *A61K 9/1635* (2013.01); *A61K 9/1652* (2013.01); *A61K 9/286* (2013.01); *A61K 9/2846* (2013.01); *A61K 9/2886* (2013.01); *A61K 9/5036* (2013.01); *A61K 9/5073* (2013.01); *A61K 9/5089* (2013.01); *A61K 31/135* (2013.01); *A61K 31/138* (2013.01); *A61K 31/522* (2013.01)

(58) Field of Classification Search
None
See application file for complete search history.

(56) References Cited

U.S. PATENT DOCUMENTS

| | | | |
|---|---|---|---|
| 4,882,169 A | 11/1989 | Ventouras | |
| 5,422,121 A | 6/1995 | Lehmann et al. | |
| 2007/0264346 A1* | 11/2007 | Guimberteau | ....... A61K 9/5073 424/488 |
| 2008/0063725 A1 | 3/2008 | Guimberteau et al. | |
| 2009/0099154 A1 | 4/2009 | Jain et al. | |
| 2011/0104266 A1 | 5/2011 | Guimberteau et al. | |
| 2012/0328697 A1 | 12/2012 | Siepmann et al. | |

FOREIGN PATENT DOCUMENTS

| | | |
|---|---|---|
| CN | 102727420 B | 1/2014 |
| EP | 0 281 513 A1 | 9/1998 |

OTHER PUBLICATIONS

Guar Gum Powder Grades, accessed online Jul. 20, 2018 (Year: 2018).*
International Search Report and Written Opinion dated Feb. 18, 2016 in PCT/EP2015/077302 Filed Nov. 23, 2015.

* cited by examiner

*Primary Examiner* — Robert A Wax
*Assistant Examiner* — Melissa S Mercier
(74) *Attorney, Agent, or Firm* — Grüneberg and Myers PLLC

(57) ABSTRACT

A pharmaceutical or nutraceutical composition, contains a) a core a), containing a pharmaceutical or a nutraceutical active ingredient and b) a coating layer b), containing a mixture of 80 to 96% by weight of a water-insoluble (meth)acrylate polymer and 4 to 20% by weight of guar gum, wherein the water-insoluble (meth)acrylate polymer contains polymerized units of more than 95 and up to 100% by weight $C_1$-$C_4$-alkyl esters of acrylic acid or of methacrylic acid and less than 5% by weight of acrylic acid or methacrylic acid.

19 Claims, No Drawings

PHARMACEUTICAL OR NUTRACEUTICAL COMPOSITION WITH RESISTANCE AGAINST THE INFLUENCE OF ETHANOL

FIELD OF THE INVENTION

The invention refers to a pharmaceutical or nutraceutical composition with sustained or extended release characteristic and with resistance against the influence of ethanol

TECHNICAL BACKGROUND

Pharmaceutical or nutraceutical compositions are designed to release the active ingredient in a manner of reproducible release curves. This shall result in desirable and reliable blood level profiles which shall provide an optimal therapeutic effect. If the blood level concentrations are too low, the active ingredient will not cause a sufficient therapeutic effect. If the blood level concentrations are too high, this may cause toxic effects. In both cases non optimal blood level concentrations of an active ingredient can be dangerous for the patient and shall therefore be avoided. A problem exists in that the ideal ratios assumed for the release of active ingredient during the design of a pharmaceutical or nutraceutical composition can be altered by the general living habits, thoughtlessness or by addictive behaviour of the patients with respect to the use of ethanol or ethanol-containing drinks. In these cases, the pharmaceutical or nutraceutical form which is actually designed for an exclusively aqueous medium is additionally exposed to an ethanol containing medium of greater or lesser strength. Since health authorities like for instance the US Food and Drug Administration (FDA) focus more and more on the ethanol problem, ethanol resistance may be an important registration requirement in the near future.

Since not all patients are aware of the risk of simultaneous taking of a controlled release pharmaceutical or nutraceutical form and ethanol-containing drinks or do not follow or are not able to follow appropriate warnings, advice or recommendations, there is a demand for controlled release pharmaceutical or nutraceutical compositions, especially for extended or sustained release pharmaceutical or nutraceutical compositions, such that their mode of action is affected as little as possible by the presence of ethanol.

Conventional extended or sustained release pharmaceutical or nutraceutical compositions if coated or uncoated are usually not resistant to alcohol at all. Several attempts have been made to provide extended or sustained release pharmaceutical or nutraceutical compositions which are resistant against the influence of ethanol.

US2007/0264346A1 describes multimicroparticulate pharmaceutical forms for oral administration. The oral pharmaceutical or dietic form comprising microparticles of the reservoir type for the modified release of at least one active principle (AP) characterized in that it is resistant to immediate dumping of the dose of AP in the presence of alcohol. The pharmaceutical form may comprise at least one agent D, which is a pharmaceutically acceptable compound whose hydration or solvation rate or capacity is greater in an alcohol-free aqueous medium than in alcoholic medium than in an alcoholic medium. Suitable agent D substances comprise a long list of substances for instance hydroxyalkyl celluloses, guar gums, carragenans, pullulans and mixtures thereof.

US2008/0063725A1 describes prolonged-release multi-microparticulate oral pharmaceutical forms. The oral pharmaceutical form comprising microparticles of the reservoir type with modified release of at least one active principle (AP) which resists immediate AP dose dumping in the presence of alcohol, and which comprises anti-misuse means. The pharmaceutical form may comprise at least one agent D, which is a pharmaceutically acceptable compound whose hydration or solvation rate or capacity is greater in an alcohol-free aqueous medium than in alcoholic medium than in an alcoholic medium. Suitable agent D substances a long list of substances for instance hydroxyalkyl celluloses, guar gums, carragenans, pullulans and mixtures thereof.

US 2012/0328697A1 describes a solid dose form comprising a film coating composition encapsulating a core, wherein: (i) the core comprises an active ingredient comprising at least one of a pharmaceutical, veterinary, or nutraceutical active ingredient; (ii) the film coating composition comprises ethylcellulose and guar gum, wherein the guar gum has an apparent viscosity ≥151.0 cps at a shear rate of 50 s−1 in a 1% aqueous guar gum solution measured rotationally at 20° C. after 1 minute equilibration using a 6 cm acrylic cone)(1° on a cone-plate viscometer wherein the shear is ramped up linearly from 1 to 50 s−1 in 25 steps over 29 seconds; (iii) the dose form provides controlled release of the active ingredient; (iv) the guar gum is present in an amount greater than 5 wt % based on the weight of the guar gum and ethylcellulose; and (v) the dose form is ethanol resistant. In the examples (p. 5, [0063]) theophylline matrix pellets are coated with different ethylcellulose (Aquacoat@ ECD):guar gum blends. The ethylcellulose (Aquacoat@ ECD) is plasticized for 1 day with 25% dibutylsebacate (DBS). Guar gum is dissolved in purified water under stirring for 2 hours. The two liquids are mixed and stirred for 30 min prior to use. The release profiles of the inventive solid dose forms in 0.1 HCl for 2 hours followed by pH buffer pH 7.4 are resistant against the influence of up to 40% ethanol in the 0.1 HCl medium.

OBJECT OF THE INVENTION

US 2012/0328697A1 describes a solid dose form comprising a film encapsulating a core where the coating is based on a mixture of plasticized ethyl cellulose and guar gum. The solid dosage form is supposed to be resistant against the influence of ethanol.

For practical uses it may be seen as disadvantage that the coating composition of solid dose forms of US 2012/0328697A1 need a comparatively long preparation time. This is mainly due to the need to plasticize ethyl cellulose which takes one day before it can be mixed and further processed with a guar gum solution.

A further disadvantage may be seen in the rather steep active ingredient release profiles of US 2012/0328697A1 even with comparatively thick coating layers which are apparently due to the combination of water-insoluble ethyl cellulose and highly water-soluble guar gum and which may be only limited suitable for active ingredients which require sustained or extended release profiles.

Thus it was an object to provide an ethanol resistant pharmaceutical or nutraceutical composition which requires only short preparation times. It was another object to provide an ethanol resistant pharmaceutical or nutraceutical composition which realizes more flat sustained or extended release profiles in comparison to the teaching of US 2012/0328697A1.

Another aspect was that presence of ethanol in concentrations of up to 40% or 40% (volume/volume) under in-vitro conditions after 2 hours at in pH 1.2 medium or in simulated gastric fluid according to USP (for instance USP 32) and subsequent change of the medium to buffered medium of pH 6.8 according to USP without ethanol should not severely influence the intended sustained or extended release rates at pH 6.8.

The objects were solved by a pharmaceutical or nutraceutical composition, comprising, comprising essentially or consisting of
  a) a core a), comprising a pharmaceutical or a nutraceutical active ingredient and
  b) a coating layer b), comprising a mixture of 80 to 96% by weight of a water-insoluble (meth)acrylate polymer and 4 to 20% by weight of guar gum,
  wherein the water-insoluble (meth)acrylate polymer is composed of polymerized units of more than 95 and up to 100% by weight $C_1$- to $C_4$-alkyl esters of acrylic acid or of methacrylic acid and less than 5% by weight of acrylic acid or methacrylic acid.

DETAILED DESCRIPTION OF THE INVENTION

The invention relates to a pharmaceutical or nutraceutical composition, comprising, comprising essentially or consisting of
  a) a core a), comprising a pharmaceutical or a nutraceutical active ingredient and
  b) a coating layer b) comprising 20 to 100, 30 to 90, 40 to 80% by weight of a mixture of 80 to 96, 85 to 96, 88 to 96, 92 to 96, 80 to 92% by weight of a water-insoluble (meth)acrylate polymer and 4 to 20, 4 to 15, 4 to 12, 4 to 8, 8 to 20% by weight of guar gum
  wherein the water-insoluble (meth)acrylate polymer is composed of polymerized units of more than 95 and up to 100% by weight $C_1$- to $C_4$-alkyl esters of acrylic acid or of methacrylic acid and less than 5% by weight of acrylic acid or methacrylic acid.

The by weight percentages of the water-insoluble (meth)acrylate polymer the guar gum add up to 100%. For example a mixture of 93% by weight of the water-insoluble (meth)acrylate polymer and 7% by weight of guar gum also corresponds to a weight ratio of 93:7 (water-insoluble (meth)acrylate polymer:guar gum).

Sustained or Extended Release Pharmaceutical or Nutraceutical Composition

The pharmaceutical or nutraceutical composition as disclosed herein is preferably a sustained release or an extended release pharmaceutical or nutraceutical composition.

The release of the pharmaceutical or nutraceutical active ingredient under in-vitro conditions in pH 1.2 medium according to USP (for instance USP 32) for 2 hours and subsequent change of the medium to buffered medium of pH 6.8 according to USP may be for instance in the range of 30 to 100, 40 to 80% including the 2 hours of the pH 1.2 phase, in a total time of 4 to 16, 4 to 12 or 4 to 8 hours.

Ethanol Resistant Pharmaceutical or Nutraceutical Composition

The pharmaceutical or nutraceutical composition as disclosed herein is an ethanol (EtOH) resistant pharmaceutical or nutraceutical composition.

The presence of ethanol in concentrations of up to 40 or 40% (volume/volume) in the gastric fluid usually leads to an undesired increase of the release rates already in the stomach which may lead to more or less undesired side effects. Thus, an effective protection against the influence of ethanol should prevent such an undesired increase of pharmaceutical or nutraceutical active ingredient in the stomach and subsequently in the intestine. On the other hand the presence of ethanol in concentrations of up to 40 or 40% (volume/volume) in the gastric fluid which may lead to a decrease of the release rates already in the stomach is seen as much less critical. In the worst case there would be no effect of the dosage form but also no undesired side effects as possible in the case of an increase. For patients which are in urgent need of a correct dose of an active ingredient it can be assumed that in most case simultaneous ethanol intake is as a rule explicitely explained and strictly forbidden by their doctor or in such a case the dosage form is anyway provided in a hospital where no ethanolic drinks should be available. However also an decrease of the active ingredient release rate may be critical in some cases and should be avoided.

Generally the presence of ethanol in concentrations of up to 40 or 40% (volume/volume) under in-vitro conditions after 2 hours in pH 1.2 medium according to (for instance USP 32) shall not severely influence the intended sustained or extended release rates at pH 1.2.

Hence there is no unique or standardized definition for an ethanol resistant pharmaceutical or nutraceutical composition. Thus the definitions given here are definitions in the sense of the invention. At least one, both of the two definitions explained as follows should be fulfilled for a pharmaceutical or nutraceutical composition to be considered as "ethanol resistant".

"Plus or Minus 20% Definition" (Definition 1)

One definition (Definition 1) for an ethanol resistant pharmaceutical or nutraceutical composition may be given in that the release of the pharmaceutical or nutraceutical active ingredient in % under in-vitro conditions in a pH 1.2 medium according to USP (for instance USP 32) with the addition of 40% (v/v) ethanol for 2 hours and subsequent buffer pH 6.8 medium (according to USP, without the addition of ethanol) does not differ by more than plus or minus 20% (absolute percentage) in the same media without addition ethanol in the pH 1.2 medium. The measurement of the values to be compared should of course take place at reasonable time intervals, preferably at time intervals of 30, 60 or 120 min.

To give an example if the intended release rate of the pharmaceutical or nutraceutical active ingredient at a certain time is in the pH 1.2 or in the pH 6.8 medium (both without ethanol) for instance 60% then the active ingredient release in the pH 1.2 medium with the addition of 40% (v/v) ethanol or in the subsequent buffer pH 6.8 medium (according to USP, without ethanol) should be no more than 80% (+20% deviation) or not less than 40% (−20% deviation). Thus the release rates in this example should be in face of the reference value 60% from/to or in between 40-80% (+/−20% deviation) for the pharmaceutical or nutraceutical composition to be considered as "ethanol resistant".

"Less Active Ingredient Release in Media with Ethanol" Definition" (Definition 2)

Another definition (Definition 2) for an ethanol resistant pharmaceutical or nutraceutical composition may be given in that the release of the pharmaceutical or nutraceutical active ingredient in % under in-vitro conditions in a pH 1.2 medium according to USP with the addition of 40% (v/v) ethanol for 2 hours and subsequent buffer pH 6.8 medium (according to USP, without the addition of ethanol) is less in the same media but without addition of ethanol in the pH 1.2 medium.

This means that the release of the pharmaceutical or nutraceutical active ingredient in % under in-vitro conditions in a pH 1.2 medium according to USP (for instance USP 32) with the addition of 40% (v/v) ethanol for 2 hours and subsequent buffer pH 6.8 medium (according to USP)

without the addition of ethanol, is, preferably at any time point or at any time point at least represented by time points of 30, 60 or by 120 min intervals, less than the release between the start time point of the release and the end time point of the release in the same media but without addition of ethanol in the pH 1.2 medium.

The start time point of the release or of the release phase is usually the time point when release can be detected short after the transfer in the pH 1.2 media (without or with ethanol) or is reasonably measured the first time in this medium. The start time point of the release phase may thus be reasonably defined as a time point from 1 to 120 min for instance at 10, 30, 60, or 120 min in the pH 1.2 medium.

The end time point of the release of the release phase may be reasonably defined as the time point when almost 100% or about 100% or 100% release (without ethanol) is reached or when the release (without ethanol) does almost no more or no more increase. The end time point of the release phase may be for instance defined as a time point at 4, 6, 8, 10 or 12 hours (total time) starting in the pH 1.2 media for 2 h and then followed by the pH 6.8 media.

In the present examples the start time point of the release is defined as 60 min and the end time point is defined as 480 or as 720 min (total time).

The corresponding release time/values may be commonly shown in the form of a release curve, which is a graph of the release values in % active ingredient measured at certain time points. If the release curve under the use of the pH 1.2 medium with the ethanol and the subsequent pH 6.8 medium is always lower than the curve in the pH 1.2 medium without the ethanol and the subsequent pH 6.8 medium this can be accepted as "ethanol resistant", because no acceleration takes place under the influence of ethanol. The release/time values may also be shown in the form of a table as in the present examples. If all corresponding release/time values in the pH 1.2 medium with the ethanol and the subsequent pH 6.8 medium are lower than the release/time with ethanol this can be accepted as well as "ethanol resistant". Of course regular and meaningful time intervals for the measurement of the release/time values should be chosen, for instance 30, 60 or 120 min intervals.

Core a)

The core a) is comprising, comprising essentially or consisting of a pharmaceutical or a nutraceutical active ingredient. The core a) may also comprise further coating layers additionally and different from the coating layer b).

The core a) may comprise a neutral carrier pellet, for instance a sugar sphere or non-pareilles, on top of which the active ingredient may be bound in a binder, such as lactose, celluloses, like micro crystalline cellulose (MCC), or polyvinylpyrrolidon (PVP). In this case the active ingredient may be bound or placed localized at the surface of the core (as a part of the core a)).

The binding of the active ingredient at the surface of the core in such a binding layer has usually no effect or influence in the sense of a release control function. Thus such a binding layer is not regarded as a release-controlling coating layer. A core a) which may comprise or consists of a neutral carrier pellet on top of which the active ingredient is bound in a binder, is regarded as an uncoated core a) in the sense of the invention.

The core a) may alternatively comprise a pellet in the form of a polymeric matrix in which the active ingredient is bound. The core a) may comprise an uncoated pellet or granule consisting of a crystallized active ingredient. The core a) may be as well an active ingredient containing tablet, a mini tablet or capsule. In these cases the active ingredient may be placed more or less randomly distributed throughout the core a) as a whole.

The core a), which may for instance comprise a neutral carrier pellet, a pellet in the form of a polymeric matrix or an uncoated pellet or granule consisting of a crystallized active ingredient, may additionally comprise one or more further polymer coating layers different from the coating layer b). Such additionally one or more further polymer coating layers are preferably release-controlling polymer coating layers, that may be, as a part of the core a), located beneath the "ethanol-resistant" coating layer b) as disclosed in here. Such additionally one or more further polymer coating layer may comprise, release controlling coating layers, such as enteric coatings or sustained release coatings, which are by themselves preferably not resistant against the influence of ethanol. Examples for such further polymer coatings are coatings out of anionic or neutral (meth)acrylate copolymers, such as EUDRAGIT® L 100-55 or EUDRAGIT® NE respectively. The one or more further coating layers as part of the core a) may also contain the active ingredient in bound form. In all these cases the core a) as a whole including its own (inner) further polymer coating will be protected by the (outer) coating layer b) which is essential for conferring ethanol resistance to the pharmaceutical or nutraceutical composition as whole. The advantage of employing cores with further polymer coatings is that together with the coating layer b) mixed active ingredient release profiles can be realized, which are at the same time resistant against the influence of ethanol.

Thus the pharmaceutical or nutraceutical composition may be characterized in that, in addition to the coating layer b), the core a) may comprise one or more further polymer coating layers.

The Coating Layer b)

The pharmaceutical or nutraceutical composition is comprising, comprising essentially or consisting of the core a) and the coating layer b).

The coating layer b) has the function of controlling the release of the active ingredient, which is placed inside the core or at the surface of the core or both. The coating layer b) has also the function of providing resistance of the active ingredient release rates against the presence ethanol.

The coating layer b), which may be called the "ethanol-resistant" coating layer, is located onto the core. A sub coat may be located between the core and the inner coating layer. A sub coat may have the function to separate substances of the core from substances of the controlling layer which may be incompatible with each other. The sub coat has essentially no influence on the active ingredient release characteristics. Preferably there is no sub coat between the core and the inner coating layer. In this case the inner coating layer is in direct contact with core.

The total amount of the coating layer b) may be in the range of 10 to 400, 15 to 200, 20 to 150, 25 to 100% by weight in relation to the weight of the core a).

The absolute amount of polymer in the coating layer b) may be in the case of pellets or granules with a size in the range of 50 to 2000, 50 to 1000 μm (average diameter) in the range of 1 to 50 preferably 2 to 40 or 2 to 30 mg/cm$^2$.

The absolute amount of polymer in the coating layer b) may be in the case of tablets with a size in the range of more than 2 and up to 25 mm (Average diameter or length) in the range of 0.5 to 20 preferably 1 to 10 mg/cm$^2$.

The coating layer b) may comprise up to 80, up to 70, up to 60, up to 50, up to 40, up to 30, up to 20, up to 10% or any (0%) by weight of pharmaceutical or nutraceutically acceptable excipients.

The pharmaceutical or nutraceutically acceptable excipients do not include a water-insoluble (meth)acrylate polymer as defined herein or guar gum. Preferably the coating layer b) comprises less than 40% by weight, less than 30% by weight, less than 10% by weight or any (0%) pharmaceutical or nutraceutically acceptable excipients.

The coating layer b) may comprise, essentially comprise or consist of 20 to 100, 30 to 90, 40 to 80% by weight of a mixture of 80 to 96, 85 to 96, 88 to 96, 92 to 96, 80 to 92% by weight of a water-insoluble (meth)acrylate polymer and 4 to 20, 4 to 15, 4 to 12, 4 to 8, 8 to 20% by weight of guar gum (the percentages add up to 100%), wherein the water-insoluble (meth)acrylate polymer is composed of free-radical polymerized units of more than 95 and up to 100% by weight $C_1$- to $C_4$-alkyl esters of acrylic acid or of methacrylic acid and less than 5% by weight of acrylic acid or methacrylic acid.

A typical coating layer b) may for example comprise or contain around 40-80% by weight of a mixture of 80-96% by weight of the water-insoluble (meth)acrylate) polymer as defined herein with 4-20% by weight of guar gum, and 60 to 20% by weight of pharmaceutical or nutraceutically acceptable excipients like glidants, for instance talc, pigments, such as yellow iron oxide, and/or preservatives, such as methyl paraben or propyl paraben.

Example for Bilayer Formulation with Coated Core a) with an Ethanol Resistant Coating Layer b)

As an example the core a) could be a pharmaceutical or nutraceutical active ingredient containing pellet comprising an sustained release polymer layer. The coating thickness could be 5 to 40% by weight in relation to the weight of the active ingredient containing pellet. Such an sustained release polymer layer could comprise for instance a water-insoluble polymer, preferably a water-insoluble polymer which is composed of free-radical polymerized units of more than 95 and up to 100% by weight $C_1$- to $C_4$-alkyl esters of acrylic or of methacrylic acid and less than 5% by weight of acrylic or methacrylic acid (EUDRAGIT® NE or NM type) preferably in combination with excipients, most preferably with a pore former excipient such as hydroxyl propyl cellulose. The amount of the pore former could be around 5 to 30% by weight in relation to the water-insoluble polymer.

Such a core a) does not release more than 10% of the active ingredient in a pH 1.2 medium according to USP (for instance USP 32, without the addition of 40% (v/v) ethanol) after 2 hours. The release rate in a pH 1.2 medium for 2 hours and subsequent buffer pH 6.8 medium may be in this case around 60-100% after total time of 6-10 hours.

However in a pH 1.2 medium according to USP (for instance USP 32) with the addition of 40% (v/v) ethanol after 2 hours the release of the active ingredient is accelerated to 60-80%. This means that the coated core a) of our example is not "ethanol resistant" and shows no more gastric resistant properties in the ethanolic medium.

To become "ethanol resistant" the core a) as described above may be coated with a coating b) as disclosed herein. Such a coating layer b) could comprise a mixture of a water-insoluble polymer which is composed of free-radical polymerized units of more than 95 and up to 100% by weight $C_1$- to $C_4$-alkyl esters of acrylic or of methacrylic acid and less than 5% by weight of acrylic acid or methacrylic acid (EUDRAGIT® NE or NM type) and guar gum as disclosed herein (for instance at a of ratio 93:7), preferably in combination with excipients, most preferably with a pore former excipient such as hydroxyl propyl cellulose. The amount of the pore former could be around 10 to 40% by weight in relation to the mixture of the water-insoluble polymer and the guar gum. The coating thickness of the coating layer b) could be around 5 to 10, 5 to 50, 20-40% by weight in relation to the weight of the core a)

The resulting pharmaceutical or nutraceutical composition shows gastric resistant properties in a pH 1.2 medium without and with the addition of 40% (v/v) ethanol and similar release rates in subsequent pH 6.8 buffer in both cases, around 60-100% after total time of 6-10 hours, and can be considered as "ethanol resistant".

Top Coat and Sub Coats

The pharmaceutical or nutraceutical composition as disclosed herein may be further coated with a sub coat or a top coat or both.

A sub coat may be part of the core a) and may be located under the coating layer b). A sub coat may have the function to separate substances of the core from substances of the controlling layer which may be incompatible with each other. The sub coat has essentially no influence on the active ingredient release characteristics. A subcoat as defined herein is therefore not regarded as a release controlling layer. A subcoat is preferably essentially water-soluble, for instance it may consist of substances like hydroxypropylmethyl-cellulose (HPMC) as a film former. The average thickness of the subcoat layer is very thin, for example not more than 15 µm, preferably not more than 10 µm.

A top coat may be located on top of the coating layer b). A top coat is also preferably essentially water soluble. A top coat may have the function of colouring the pharmaceutical or nutraceutical form or protecting from environmental influences for instance from moisture during storage. The top coat may consist out of a binder, for instance a water soluble polymer like a polysaccharide or HPMC, or a sugar compound like saccharose. The top coat may further contain pharmaceutical or nutraceutical excipients like pigments or glidants in high amounts. The topcoat has essentially no influence on the release characteristics.

The expressions sub coat and top coat are well known to the person skilled in the art.

The pharmaceutical or nutraceutical composition may be preferably characterized in that there are except for the coating layer b) comprising the water-insoluble (meth)acrylate polymer and the guar gum no further controlling layers present which control the release the pharmaceutical or a nutraceutical active ingredient.

The Water-insoluble (Meth)Acrylate Polymers

The term "a water-insoluble (meth)acrylate polymer" in the sense of the invention shall be understood as "at least one water-insoluble (meth)acrylate polymer" and may thus cover the presence one or more water-insoluble polymers and shall include homopolymers as well as copolymers, which do not dissolve in water and which are only swellable in water over of the whole range of pH 1-14.

EUDRAGIT® NE 30D/EUDRAGIT® NM 30D-type Polymers

The coating layer b) comprises a water-insoluble (meth) acrylate polymer which is composed of (free-radical) polymerized units of more than 95 and up to 100% by weight $C_1$- to $C_4$-alkyl esters of acrylic acid or of methacrylic acid and less than 5% by weight of acrylic acid or methacrylic acid. These kinds of polymers do not dissolve in water or are only swellable in water over of the whole range of pH 1-14.

Suitable $C_1$- to $C_4$-alkyl esters of acrylic acid or of methacrylic are, for example, methyl methacrylate, ethyl methacrylate, butyl methacrylate, methyl acrylate, ethyl acrylate and butyl acrylate. Preference is given to methyl methacrylate, ethyl acrylate and methyl acrylate.

Methacrylate monomers with anionic radicals, for example acrylic acid and/or methacrylic acid, may be present in small amounts of less than 5, less than 4, less than 3, less than 2 or less than 1% by weight, preferably by no more than 1% by weight or by 0.05 to 1 or by 0 to 0.5% by weight. Preferably no methacrylate monomers with anionic radicals are contained.

Suitable examples of water-insoluble (meth)acrylate polymers are copolymers composed of 20 to 40% by weight of ethyl acrylate, 60 to 80% by weight of methyl methacrylate and 0 to less than 5% by weight, preferably 0 to 2 or 0.05 to 1% or by 0 to 0.5% by weight of methacrylic acid or any methacrylic acid (EUDRAGIT® NE 30D or EUDRAGIT® NM 30D type).

EUDRAGIT® NE 30D and Eudragit® NM 30D are dispersions containing 30% by weight of copolymers composed of free-radically polymerized units of 30% by weight of ethyl acrylate and 70% by weight of methyl methacrylate.

Preference is given to neutral or essentially neutral methyl acrylate copolymers which, according to WO 01/68767, have been prepared as dispersions using 1-10% by weight of a nonionic emulsifier having an HLB value of 15.2 to 17.3. The latter offer the advantage that there is no phase separation with formation of crystal structures by the emulsifier (Eudragit® NM 30D type).

According to EP 1 571 164 A2, corresponding, virtually neutral (meth)acrylate copolymers with small proportions of 0.05 to 1% by weight of monoolefinically unsaturated C3-C8-carboxylic acids can, however, also be prepared by emulsion polymerization in the presence of comparatively small amounts of anionic emulsifiers, for example 0.001 to 1% by weight.

Guar Gum

Guar gum is a natural polysaccharide, which is extracted from the seeds of the annual legume *Cyamopsis tretragonolobus* (trivial names: Guar or cluster bean, Gavar, Guwar or Guvar). Guar gum is a galactomannan, which is water-soluble and exhibits a viscosifying effect in water. The term Guar gum in the sense of the invention shall include all qualities of Guar gum. Thus it includes high molecular weight natural Guar gum as well as processed guar gum such as partially hydrolysed guar gum (PHGG) which has a comparably low molecular weight (Mw) of around 20.000-30.000 Daltons.

Analytical methods to determine the molecular weight ($M_w$=average weight molecular weight) are well known to a skilled person. In general molecular weight $M_w$ can be determined by gel permeation chromatography or by a light-scattering method (see, for example, H. F. Mark et al., Encyclopedia of Polymer Science and Engineering, 2nd Edition, Vol. 10, pages 1 ff., J. Wiley, 1989).

Viscosity

A suitable type of guar gum have a viscosity of 100 to 5,000, 500 to 4,500 centipoise (cp) of a 1% aqueous solution (weight /weight) at 25° C.

The methodology of determination of the viscosity of a polymer solution, for instance a solution of Guar gum, is well known to the skilled person. The test is performed using a spindle viscometer.

The viscosity of a 1% Guar gum may be determined by adding 5 g product to 445 g of distilled water in a beaker while stirring at about 1500 rpm using overhead stirrer. Then additional 50 g water was added with rinsing the walls of the beaker. After stirring for 1 hours and getting a complete solution, the viscosity is measured using a LV model of the Brookfield viscometer at 25° C. using suitable spindle. For example viscosity of guar gum high viscosity (4219 cps) and guar gum medium viscosity (2000 cps) was determined at 12 rpm with spindle LV-3(63) using Brookfield viscometer model no. LVDV-II+P. Theoretically possible marginal differences are regarded as insignificant.

Sustained or Extended Release

A general definition for Extended release or Sustained release is given under "Nomenclature guidelines for USP on page number 6 and 7" as Extended-Release—Extended-release products are formulated in such a manner as to make the drug substance available over an extended period of time following ingestion.

A typical, pharmaceutical or nutraceutical composition is preferably of the type of sustained or extended release form and may be characterized in that the release of the pharmaceutical or nutraceutical active under in-vitro conditions after 2 hours in pH 1.2 medium and subsequent change of the medium to buffered medium of pH 6.8 (according to USP) is 30 to 90, 40 to 80 or 70-100% in a total time from 4 to 16 or 4 to 12, 4 to 8 or 8-12 hours. The term "total time" in this case shall include the 2 hours pH 1.2 phase. Thus a "total time" of 4 hours shall mean 2 hours at pH 1.2 plus 2 hours at pH 6.8. In the enteric release form the release after 2 hours in pH 1.2 medium is 10% or less.

Pharmaceutical or Nutraceutical Active Ingredient

The inventive composition is comprising a pharmaceutical or a nutraceutical active ingredient. Therefore the inventive composition is a pharmaceutical or a nutraceutical composition. The inventive composition is preferably a sustained or extended release pharmaceutical or nutraceutical composition comprising a core a), comprising a pharmaceutical or nutraceutical active ingredient. Preferably the core a) may comprise 1-100, 2-80, 5-75, 10-50% by weight of a pharmaceutical or a nutraceutical active ingredient.

Nutraceutical Active Ingredients

The inventive composition is preferably useful for a nutraceutical compositions or nutraceutical dosage forms (neutraceuticals). Nutraceuticals or nutraceutical active ingredients can be defined as extracts of foods claimed to have medical effects on human health. The nutraceutical is usual contained in a medical format such as capsule, tablet or powder in a prescribed dose. Examples for nutraceuticals are resveratrol from grape products as an antioxidant, soluble dietary fiber products, such as psyllium seed husk for reducing hypercholesterolemia, broccoli (sulphane) as a cancer preservative, and soy or clover (isoflavonoids) to improve arterial health. Other nutraceuticals examples are flavonoids, antioxidants, alpha-linoleic acid from flax seed, beta-carotene from marigold petals or fish oil. Sometimes the expression neutraceuticals is used as synonym for nutraceuticals.

Pharmaceutical Active Ingredients

The inventive composition is preferably useful for a pharmaceutical compositions or pharmaceutical dosage forms (pharmaceuticals). The invention is preferably useful for sustained release formulated pharmaceutical compositions or pharmaceutical dosage forms.

The therapeutical and chemical classes of pharmaceutical active ingredients (drugs) used in sustained or extended release formulated coated pharmaceutical dosage forms are for instance analgetics, antibiotics or anti-infectives, antibodies, antiepileptics, antigens from plants, antirheumatics, betablocker, benzimidazole derivatives, beta-blocker, cardiovascular drugs, chemotherapeutics, CNS drugs, digitalis glycosides, gastrointestinal drugs, e.g. proton pum inhibitors, enzymes, hormons, liquid or solid natural extracts, oligonucleotides, peptidhormon proteins, therapeutical bacteria, peptides, proteins, proton pump inhibitors, (metal)salt f.e. aspartates, chlorides, orthates, urology drugs, vaccines Further examples of drugs for sustained or extended controlled release may be: acamprosat, aescin, amylase, acetylsalicyclic acid, adrenalin, 5-amino salicyclic acid, aureomycin, bacitracin, balsalazine, beta carotene, bicalutamid bisacodyl, bromelain, bromelain, budesonide, calcitonin, carbamacipine, carboplatin, cephalosporins, cetrorelix, clarithromycin,chloromycetin, cimetidine, cisapride, cladribine, clorazepate, cromalyn, 1-deaminocysteine-8-D-arginine-vasopressin, deramciclane, detirelix, dexlansoprazole, diclofenac, didanosine, digitoxin and other digitalis glycosides, dihydrostreptomycin, dimethicone, divalproex, drospirenone,duloxetine, enzymes, erythromycin, esomeprazole, estrogens, etoposide, famotidine, fluorides, garlic oil, glucagon, granulocyte colony stimulating factor (G-CSF), heparin, hydrocortisone, human growth hormon (hGH), ibuprofen, ilaprazole, insulin, Interferon, Interleukin, Intron A, ketoprofen, lansoprazole, leuprolidacetat lipase, lipoic acid, lithium, kinin, memantine, mesalazine, methenamine, milameline, minerals, minoprazole, naproxen, natamycin, nitrofurantion, novobiocin, olsalazine, omeprazole, orothates, pancreatin, pantoprazole, parathyroidhormone, paroxetine, penicillin, perprazol, pindolol, polymyxin, potassium, pravastatin, prednisone, preglumetacin progabide, pro-somatostatin, protease, quinapril, rabeprazole, ranitidine, ranolazine, reboxetine, rutosid, somatostatin streptomycin, subtilin, sulfasalazine, sulphanilamide, tamsulosin, tenatoprazole, thrypsine, valproic acid, vasopressin, vitamins, zinc.

Further examples are Buproprion HCl, Carvedilol phosphate, Clonidine, Cyclobezaprine HCl, Codeine, Dalfampridine, Desvenlafaxine succinate, Dexmethylphenidate HCl, Fesoterodine fumarate, Gabapentin enacarbil, Lamotrigine, Levetiracetin, Memantine HCl, Metformin HCl, Saxagliptin, Metoprolol Succinate, Morphine sulphate, naltreoxzone, Oxycodone HCl, Oxymorphone HCl, Pramipexole dihydrochloride, Quetiapine fumarate, Ropinirole HCl, Tapentadol HCl, Tramodol HCl, Trazodone HCl, Trospium Chloride, Venlafaxine HCl, Thyophylline, Diprophylline including their salts, derivatives, polymorphs, isomorphs, or any kinds of mixtures or combinations thereof.

Pharmaceutical or Nutraceutical Composition

The pharmaceutical or nutraceutical composition as disclosed herein may be included in or may be present in the form of a tablet, a minitablet, a pellet, a granule, a sachet or a capsule. A capsule for instance may be filled with the inventive composition in the form of coated pellets or with coated granules, where "coated" means at least coated with coating layer b). In another embodiment a capsule coated itself with a coating layer b) may filled with coated or uncoated pellets, with a powder or with coated or uncoated granules.

The term tablet includes pellet-containing tablets or compressed tablets and is well known to a skilled person. Such a tablet may have a size of more than 4, around 5 to 25 mm for instance. Usually, defined pluralities of small active ingredient containing pellets are compressed therein together with binding excipients to give the well known tablet form. After oral ingestion and contact with the body fluid the tablet form is disrupted and the pellets are set free. The compressed tablet combines the advantage of the single dose form for ingestion with the advantages of a multiple forms, for instance the dosage accuracy.

The term minitablet is well known to the skilled person. A minitablet is smaller than the traditional tablet and may have a size of around 1 to 4 mm. The minitablet is, like a pellet, a single dosage form to be used in multiple dosages. In comparison to pellets, which may be in the same size, minitablets usually have the advantage of having more regular surfaces which can be coated more accurately and more uniformly. Minitablets may be provided enclosed in capsules, such as gelatine capsules. Such capsules disrupt after oral ingestion and contact with the gastric or intestinal fluids and the minitablets are set free. Another application of minitablets is the individual fine adjustment of the active ingredient dosage. In this case the patient may ingest a defined number of minitablets directly which matches to the severe of the decease to cure but also to his individual body weight. A minitablet is different from pellet-containing compressed tablet as discussed above.

The term sachet is well known to the skilled person. It refers to small sealed package which contains the active ingredient often in pellet containing liquid form or also in dry pellet or powder form. The sachet itself is only the package form is not intended to be ingested. The content of the sachet may be dissolved in water or as an advantageous feature may be soaked or ingested directly without further liquid. The latter is advantageous feature for the patient when the dosage form shall be ingested in a situation where no water is available. The sachet is an alternative dosage form to tablets, minitablets or capsules.

The preferably extended or sustained release pharmaceutical or nutraceutical coating composition is preferably present in the form of an aqueous coating solution, suspension or dispersion. The dry weight content of such a solution, suspension or dispersion may be in the range of 10 to 50, preferably 15 to 35%.

Pharmaceutical or Nutraceutically Acceptable Excipients

Pharmaceutical or nutraceutically acceptable excipients are excipients which are well known to a skilled person and frequently used in the field of pharmacy and galenics as processing or formulation auxiliaries. Pharmaceutical or nutraceutically acceptable means that the excipients are not harmful or toxic and are allowed to be used in pharmaceutical or nutraceutical compositions.

The Pharmaceutical or nutraceutical composition may comprise pharmaceutical or nutraceutically acceptable excipients selected from the group of antioxidants, brighteners, binding agents, flavouring agents, flow aids, fragrances, glidants, penetration-promoting agents, pigments, plasticizers, polymers which are different from the water-insoluble polymer as defined herein and different from guar gum, pore-forming agents or stabilizers or combinations thereof. The pharmaceutical or nutraceutically acceptable excipients may be comprised in the core a) and/or in the coating layer b).

The coating layer may comprise up to 80, up to 70, up to 60, up to 50, up to 40, up to 30, up to 20, up to 10% by weight or 0-40, 5-35, 10-30% or any (0%) by weight of pharmaceutical or nutraceutically acceptable excipients Pharmaceutical or nutraceutically acceptable excipients may be selected from the group of antioxidants, brighteners, binding agents, flavouring agents, flow aids, fragrances, glidants, penetration-promoting agents, polymers (preferably different from the water-insoluble polymer as defined herein and different from guar gum; excipient polymers can be for instance disintegrants like polyvinyl pyrrolidone), pigments, plasticizers, pore-forming agents (including pore forming polymers, such as hydroxyl propyl cellulose (HPC) or stabilizers or any combinations thereof.

Preferably the pharmaceutical or nutraceutically acceptable excipients do not include polymers, except for hydroxyl propyl cellulose or except for pore-forming polymers. In some embodiments the pharmaceutical or nutraceutically acceptable excipients may not include polymers at all.

Addition of Further Polymers to the Coating Layer b)

The coating layer b) of the pharmaceutical or nutraceutical composition may further comprise pharmaceutical or nutraceutically acceptable excipients which may be called further polymer, one or more polymers or copolymers, preferably water-soluble polymers or copolymers, with neutral or ionic side groups, which polymers or copolymers which are different from the water-insoluble (meth)acrylate polymers and the guar gum. For instance one or more of such additional or further polymers or copolymers with neutral or ionic side groups respectively may be comprised or contained in the coating layer b) as long as the properties of the pharmaceutical or nutraceutical composition as disclosed herein are not influenced negatively.

Further polymers or copolymers with neutral or ionic side groups which may be comprised or contained additionally the inner or to the outer coating layer may belong to the groups of celluloses, alkyl celluloses, anionic celluloses, anionic vinyl polymers or anionic (meth)acrylate copolymers.

Water-soluble celluloses may be preferably selected from the group of water-soluble methyl-, ethyl or propyl-ethers of cellulose or any combinations thereof. Water-soluble celluloses may be are selected from the group of methyl celluloses, hydroxy-methyl-celluloses, hydroxyl-ethyl-celluloses, hydroxyl-ethyl-methyl-celluloses, hydroxyl-propyl-celluloses (HPC), hydroxyl-methyl-propyl-celluloses (HPMC), ethyl-hydroxy-ethyl-celluoses, carboxy-methyl-celluloses, carboxy-methyl-ethyl celluloses, sodium-carboxy-methyl-celluloses or any combinations thereof.

Usually the coating layer may comprise or contain less than 10, less than 5, less than 2, less than 1% by weight or any (0%) of these further polymers or copolymers with neutral or ionic side groups respectively calculated either on the content of the mixture of the water-insoluble polymer as defined herein and the guar gum in the inner coating layer. As a rule it is preferred that the inner coating layer and/or the outer coating layer of the pharmaceutical or nutraceutical composition do not comprise or contain any of such additional further polymers or copolymers.

Polyvinylpyrrolidones as Further Polymers

The coating layer b) may comprise one or more water-soluble polyvinylpyrrolidones as further polymers. The preferred molecular weight (Mw) of water-soluble polyvinylpyrrolidones may be in the range of 2.500-2.500.000, 5.000-250.000, 10.000-50.000 g/mol. Analytical methods to determine the molecular weight ($M_w$=average weight molecular weight) are well known to a skilled person. In general molecular weight $M_w$ can be determined by gel permeation chromatography or by a light-scattering method (see, for example, H. F. Mark et al., Encyclopedia of Polymer Science and Engineering, 2nd Edition, Vol. 10, pages 1 ff., J. Wiley, 1989). Preferably the coating layer may comprise or contain less than 10, less than 5, less than 2, less than 1% by weight or any (0%) of one or more water-soluble polyvinylpyrrolidones.

Neutral Celluloses as Further Polymers

Examples for suitable neutral celluloses are microcrystalline cellulose, ethyl cellulose, hydroxyethyl cellulose (HEC), hydroxypropyl cellulose (HPC) or hydroxypropyl methylcellulose (HPMC). Neutral water-soluble celluloses may be preferably selected from the group of water-soluble methyl-, ethyl or propyl-ethers of cellulose or any combinations thereof.

Water-soluble celluloses may be are selected from the group of methyl celluloses, hydroxy-methyl-celluloses, hydroxyl-ethyl-celluloses, hydroxyl-ethyl-methyl-celluloses, hydroxyl-propyl-celluloses (HPC), hydroxyl-methyl-propyl-celluloses (HPMC), ethyl-hydroxy-ethyl-celluoses, carboxy-methyl-celluloses, carboxy-methyl-ethyl celluloses, sodium-carboxy-methyl-celluloses or any combinations thereof.

Preferably the coating layer b) may comprise or contain less than 10, less than 5, less than 2, less than 1% by weight or any (0%) of neutral or neutral water-soluble celluloses.

Anionic Celluloses as Further Polymers

Suitable anionic polymer or copolymers may be carboxymethyl cellulose and its salts (CMC, Na-CMC, Blanose®, Tylopur®), carboxymethylethyl cellulose and its salts, cellulose acetate phthalate (CAP), cellulose acetate succinate (CAS), cellulose acetate trimelliate (CAT), hydroxypropyl methyl cellulose phthalate (HPMCP, HP50, HP55) or hydroxypropylmethyl cellulose acetate succinate (HPMCAS-LF, -MF, -HF). Preferably the coating layer may comprise or contain less than 10, less than 5, less than 2, less than 1% by weight or any (0%) of anionic celluloses.

Anionic Polyvinyl Polymers as Further Polymers

Suitable polyvinyl polymers or copolymers may comprise structural units that are derived from unsaturated carboxylic acids other than acrylic acid or methacrylic acid as exemplified by polyvinylacetate-phthalate, a copolymer of vinylacetate and crotonic acid 9:1 or polyvinylacetate-succinate. Preferably the coating layer may comprise or contain less than 10, less than 5, less than 2, less than 1% by weight or any (0%) of polyvinyl polymers or copolymers.

Anionic (Meth)Acrylate Copolymers as Further Polymers

Suitable anionic (meth)acrylate copolymers may comprise 25 to 95, preferably 40 to 95, in particular 60 to 40, % by weight free-radical polymerized $C_1$- to $C_{18}$-alkyl esters, preferably $C_1$- to $C_8$- or $C_1$- to $C_4$-alkyl esters alkyl esters of acrylic or of methacrylic acid and 75 to 5, preferably 60 to 5, in particular 40 to 60, % by weight (meth)acrylate monomers having an anionic group.

The monomer proportions mentioned normally add up to 100% by weight. However it is also possible in addition, without this leading to an impairment or alteration of the essential properties, for small amounts in the region of 0 to 10, for example 1 to 5, % by weight of further monomers capable of vinylic copolymerization, such as, for example, hydroxyethyl methacrylate or hydroxy-ethyl acrylate, to be present. It is preferred that no further monomers capable of vinylic copoly-merization are present.

$C_1$- to $C_4$-alkyl esters of acrylic or methacrylic acid are in particular methyl methacrylate, ethyl methacrylate, butyl methacrylate, methyl acrylate, ethyl acrylate and butyl acrylate.

Preferably the coating layer may comprise or contain less than 10, less than 5, less than 2, less than 1% by weight or any (0%) of anionic (meth)acrylate copolymers.

Process for Producing a Pharmaceutical or Nutraceutical Form

A suitable process for producing the pharmaceutical or nutraceutical composition as disclosed in here may be by forming the core a) comprising the pharmaceutical or nutraceutical active ingredient by direct compression, compression of dry, wet or sintered granules, by extrusion and subsequent rounding off, by wet or dry granulation, by direct pelleting or by binding powders onto active ingredient-free beads or neutral cores or active ingredient-containing particles and by applying the coating layer b) in the form of aqueous dispersions or organic solutions in spray processes or by fluidized bed spray granulation.

Pellet/Granule/Tablet/Minitablet/Sachet/Capsule

Pharmaceutical or nutraceutical composition may be a coated tablet, a coated minitablet, a coated pellet, a coated granule, a sachet, a capsule, filled with coated pellets or with powder or with granules, or a coated capsule.

Pellets or granules may be used as cores or in compressed tablets. As a rough estimation pellets may have a size in range of 50 to 2000, 50 to 1000 µm (average diameter) while coated tablets may have a size in the range of more than 2 and up to 25 mm (Average diameter or length). As a rule one can say the smaller the size of the pellet cores are, the higher is the pellet coating weight gain needed. This is due to the comparably higher surface area of pellets compared to tablets.

The term pellet-containing tablet or compressed tablet is well known to a skilled person. Such a tablet may have a size of around 5 to 25 mm for instance. Usually, defined pluralities of small active ingredient containing pellets are compressed therein together with binding excipients to give the well known tablet form. After oral ingestion and contact with the body fluid the tablet form is disrupted and the pellets are set free. The compressed tablet combines the advantage of the single dose form for ingestion with the advantages of a multiple forms, for instance the dosage accuracy. In tablets coatings comparably low amounts of excipients, preferably talcum but also other excipients, may be used in contrast to pellets.

The term minitablet is well known to the skilled person. A minitablet is smaller than the traditional tablet and may have a size of around 1 to 4 mm. The minitablet is, like a pellet, a single dosage form to be used in multiple dosages. In comparison to pellets, which may be in the same size, minitablets usually have the advantage of having more regular surfaces which can be coated more accurately and more uniformly. Minitablets may be provided enclosed in capsules, such as gelatine capsules. Such capsules disrupt after oral ingestion and contact with the gastric or intestinal fluids and the minitablets are set free. Another application of minitablets is the individual fine adjustment of the active ingredient dosage. In this case the patient may ingest a defined number of minitablets directly which matches to the severe of the decease to cure but also to his individual body weight. A minitablet is different from pellet-containing compressed tablet as discussed above.

The term sachet is well known to the skilled person. It refers to small sealed package which contains the active ingredient often in pellet containing liquid form or also in dry pellet or powder form. The sachet itself is only the package form is not intended to be ingested. The content of the sachet may be dissolved in water or as an advantageous feature may be soaked or ingested directly without further liquid. The latter is advantageous feature for the patient when the dosage form shall be ingested in a situation where no water is available. The sachet is an alternative dosage form to tablets, minitablets or capsules.

The term capsule is well known to the skilled person. A capsule is like the sachet a container for pellets containing liquids or also dry pellets or powders. However in contrast to the sachet the capsule consists of pharmaceutically acceptable excipients such as gelatine or hydroxypropylmethylcellulose (HPMC) and is intended to be ingested like a tablet. The capsules disrupts after oral ingestion and contact with the gastric or intestinal fluids and the contained multiple units are set free. Capsules for pharmaceutical purposes are commercially available in different standardized sizes.

Use

The pharmaceutical or nutraceutical composition as described herein may be used as enteric release, sustained release or extended release pharmaceutical or nutraceutical composition with resistance against the influence of ethanol. The terms "enteric release", "sustained release" and "extended release" are well known to a skilled person.

EXAMPLES

Analytical Methodology
1. Dissolution Method for Metoprolol Succinate
The dissolution of Metoprolol succinate pellets was detected chromatographically.
Chromatographic Condition
Column: Agilent Zorbax C8 column, 150×4.6 mm, 5µm or equivalent
Column Temp: 25° C.
Sample Temp.: 25° C.
Mobile Phase: Buffer: Acetonitrile (750:250)
Injection volume: 20 µL
Wavelength: 280 nm
Run time: 10.0 minutes
Retention time: About 3.0 min.
Label claim: 190 mg
Gradient Flow

| Minute | Flow (mL/min) | % Mobile phase |
|---|---|---|
| 0.0 | 1.0 | 100 |
| 5.5 | 1.0 | 100 |
| 6.5 | 1.5 | 100 |
| 9 | 1.5 | 100 |
| 10 | 1.0 | 100 |

Preparation of Buffer
Weighed and transferred 9 gms of Monobasic Sodium Phosphate (NaH2PO4.H2O) to 1000 ml of water, sonicated to dissolve the salt. 8.0 ml of 1 M Ortho Phosphoric Acid was added to it and adjusted pH to 3.0 (±0.05) with 1 M monobasic sodium phosphate or Ortho Phosphoric Acid. Filtered the buffer through 0.45 µm Nylon 6.6 membrane filter.
Dissolution Parameters
Acid Stage
Apparatus: USP-II (Paddle)
Volume: 900 mL
Dissolution Media: 0.1 N HCl/40% Alcoholic HCl
Temperature: 37.0° C.±0.5° C.
RPM: 50
Buffer Stage
Apparatus: USP-II (Paddle)
Volume: 500 mL
Dissolution Media: pH 6.8 Phosphate buffer
Temperature: 37.0° C.±0.5° C.
RPM: 50
Dissolution Media
Preparation of 0.1 N HCl:
About 8.8 ml of Concentrated HCl was diluted to 1000 ml with water.
Preparation of 40% Alcoholic 0.1 N HCl:
400 ml of Ethanol was added to 550 ml of water. To this solution 8.8 ml of Concentrated HCl was added and then volume was made up to the 1000 ml mark and mixed.

Preparation of pH 6.8 Buffer 6.8 g of Potassium Dihydrogen Phosphate and 0.89 g of sodium hydroxide were transferred into 1000 ml of water and mixed. The pH was adjusted to 6.8±0.05 with 0.2 M sodium hydroxide solution.

Preparation of Stock Solution 47.5 mg of Metoprolol succinate working standard were transferred into a 50 ml volumetric flask. Added about 25 ml of Methanol and sonicated to dissolve then volume was made up to the 50 ml mark with water. 10 ml of this solution was diluted to 25 ml with dissolution media.

Preparation of Standard Solution in pH 6.8 Buffer 10 ml of stock solution was diluted to 25 ml with dissolution media.

Preparation of Standard Solution in 0.1 N HCl and 40% Alcoholic HCl 5 ml of stock solution was diluted to 25 ml with dissolution media.

Preparation of Sample Solution

Weighed and transferred each 190 mg equivalent of Metoprolol succinate pellets in six dissolution jars and performed the dissolution test as per parameters given in the method above. This sample solution was filtered through 0.45 μm nylon membrane syringe filter discarded first 2 mL of the filtrate. Filtrate was used as sample.

Procedure

The dissolution apparatus was set as per parameters. Transferred 190 mg equivalent of Metoprolol succinate and carried out the dissolution.

2. Dissolution Method for Theophylline Pellets

The dissolution of Theophylline was detected chromatographically.

Chromatographic Conditions

Column: Agilent Zorbax C18 column, 150×4.6 mm, 5μm or equivalent
Column Temp: 25° C.
Sample Temp.: 25° C.
Mobile Phase: Water: Methanol: Glacial acetic acid (64:35:1)
Injection volume: 10 μL
Flow: 1.0 mL/min
Wavelength: 254 nm
Run time: 5.0 minutes
Retension time: About 2.5 min.
Label claim: 100 mg
Dissolution Parameters
Acid Stage
Apparatus: USP-II (Paddle)
Volume: 900 mL
Dissolution Media: 0.1 N HCl/40% Alcoholic HCl
Temperature: 37.0° C.±0.5° C.
RPM: 50
Buffer Stage
Apparatus: USP-II (Paddle)
Volume: 900 mL
Dissolution Media: pH 6.8 Phosphate buffer
Temperature: 37.0° C.±0.5° C.
RPM: 50

Preparation of Dissolution Media:
Preparation of 0.1 N HCl (According to USP)

About 8.8 ml of Concentrated HCl was diluted to 1000 ml with water.

Preparation of 40% Alcoholic 0.1 N HCl:

400 ml of Ethanol was added to 550 ml of water. To this solution 8.8 ml of Concentrated HCl was added and then volume was made up to the 1000 ml mark and mixed.

Preparation of pH 6.8 Buffer (USP Media)

Weighed accurately about 6.8 g of Potassium Dihydrogen Phosphate and 0.89 g of sodium hydroxide and transferred it into 1000 ml of water and mixed. The pH was adjusted to 6.8±0.05 with 0.2 M sodium hydroxide solution.

Preparation of Standard Solution 50.0 mg Theophylline working standard was transferred into a 50 ml volumetric flask. About 25 ml of methanol were added and sonicated to dissolve then volume was made up to the 50 ml mark with methanol. 5 ml of this solution was diluted to 50 ml with dissolution media.

Preparation of Sample Solution

Pellets equivalent to 100 mg of Theophylline were transferred in six dissolution jars and performed the dissolution test as per parameters given in the method above. This sample solution was filtered through 0.45 μm nylon membrane syringe filter discarded first 2 mL of the filtrate. Filtrate was used as sample.

Procedure

The dissolution apparatus was set as per parameters. Pellets equivalent to 100 mg of Theophylline was added in each dissolution vessel and the dissolution test was carried out.

3. Dissolution Method for Tramadol HCl Pellets

The dissolution of Tramadol HCl was detected chromatographically.

Chromatographic Conditions

Column: Agilent Zorbax C8 column, 150×4.6 mm, 5μm or equivalent
Column Temp: 25° C.
Sample Temp.: 25° C.
Mobile Phase: Buffer: Acetonitrile (60:40)
Injection volume: 20 μL
Flow: 1.0 mL/min
Wavelength: 273 nm
Run time: 6.0 minutes
Retension time: About 3.1 min.
Label claim: 100 mg
Dissolution Parameters
Acid Stage
Apparatus: USP-II (Paddle)
Volume: 900 mL
Dissolution Media: 0.1 N HCl/40% Alcoholic HCl
Temperature: 37.0° C.±0.5° C.
RPM: 50
Buffer Stage
Apparatus: USP-II (Paddle)
Volume: 900 mL
Dissolution Media: pH 6.8 Phosphate buffer
Temperature: 37.0° C.±0.5° C.
RPM: 50

Preparation of Dissolution Media:
Preparation of 0.1 N HCl (According to USP)

About 8.8 ml of Concentrated HCl was diluted to 1000 ml with water.

Preparation of 40% Alcoholic 0.1 N HCl:

400 ml of Ethanol was added to 550 ml of water. To this solution 8.8 ml of Concentrated HCl was added and then volume was made up to the 1000 ml mark and mixed.

Preparation of pH 6.8 Buffer (USP Media)

Weighed accurately about 6.8 g of Potassium Dihydrogen Phosphate and 0.89 g of sodium hydroxide and transferred it into 1000 ml of water and mixed. The pH was adjusted to 6.8±0.05 with 0.2 M sodium hydroxide solution.

Preparation of Standard Solution

Weighed accurately about 55.0 mg of Tramadol HCl working standard and transferred into a 50 ml volumetric flask. Added about 25 ml of 0.1 N HCl and sonicated to dissolve then volume was made up to the mark with 0.1 N HCl. 5 ml of this solution was diluted to 50 ml with dissolution media.

Preparation of Sample Solution

Pellets equivalent to 100 mg of Tramadol HCl were transferred in six dissolution jars and performed the dissolution test as per parameters given in the method above. This sample solution was filtered through 0.45 µm nylon membrane syringe filter discarded first 2 mL of the filtrate. Filtrate was used as sample.

Procedure

The dissolution apparatus was set as per parameters. Pellets equivalent to 100 mg of Tramadol HCl was added in each dissolution vessel and the dissolution test was carried out.

4. Dissolution Method for Diprophylline Pellets

The dissolution of Diprophylline was detected chromatographically.

Chromatographic Conditions

Column: Agilent Zorbax C18 column, 150×4.6 mm, 5 µm or equivalent
Column Temp: 25° C.
Sample Temp.: 25° C.
Mobile Phase: Mobile phase A: Mobile phase B
Injection volume: 10 µL
Flow: 1.0 mL/min
Wavelength: 254 nm
Run time: 8.0 minutes
Retension time: About 2.4 min.
Label claim: 200 mg
Mobile Phase Preparation:
Mobile Phase A:
Buffer: Methanol mixed in a ratio 675:325.
Buffer Preparation:

Accurately weighed and dissolved 1.04 g of Potassium di-hydrogen phosphate in 1000 mL of water and adjusted the pH of the solution to 4.5±0.05 with ortho-phosphoric acid. The buffer was filtered through 0.45 µm Nylon 6.6 membrane filter.

Mobile Phase B:
Methanol.
Gradient Flow

| Minute | Flow (mL/min) | % Mobile phase A | % Mobile phase B |
|---|---|---|---|
| 0.00 | 1.0 | 100 | 0 |
| 3.50 | 1.0 | 100 | 0 |
| 3.51 | 1.4 | 75 | 25 |
| 4.80 | 1.4 | 75 | 25 |
| 4.81 | 1.0 | 100 | 0 |
| 8.00 | 1.0 | 100 | 0 |

Dissolution Parameters
Acid Stage
Apparatus: USP-II (Paddle)
Volume: 900 mL
Dissolution Media: 0.1 N HCl/40% Alcoholic HCl
Temperature: 37.0° C.±0.5° C.
RPM: 50
Buffer Stage
Apparatus: USP-II (Paddle)
Volume: 900 mL
Dissolution Media: pH 6.8 Phosphate buffer
Temperature: 37.0° C.±0.5° C.
RPM: 50
Preparation of Dissolution Media:
Preparation of 0.1 N HCl (According to USP)
About 8.8 ml of Concentrated HCl was diluted to 1000 ml with water.
Preparation of 40% Alcoholic 0.1 N HCl:
400 ml of Ethanol was added to 550 ml of water. To this solution 8.8 ml of Concentrated HCl was added and then volume was made up to the 1000 ml mark and mixed.
Preparation of pH 6.8 Buffer (USP Media)

Weighed accurately about 6.8 g of Potassium Dihydrogen Phosphate and 0.89 g of sodium hydroxide and transferred it into 1000 ml of water and mixed. The pH was adjusted to 6.8±0.05 with 0.2 M sodium hydroxide solution.

Preparation of Standard Solution

Weighed accurately about 50.0 mg of Diprophylline working standard and transferred into a 50 ml volumetric flask. Added about 25 ml of water and sonicated to dissolve then volume was made up to the mark with water. 5 ml of this solution was diluted to 25 ml with dissolution media.

Preparation of Sample Solution

Pellets equivalent to 200 mg of Diprophylline were transferred in six dissolution jars and performed the dissolution test as per parameters given in the method above. This sample solution was filtered through 0.45 µm nylon membrane syringe filter discarded first 2 mL of the filtrate. Filtrate was used as sample.

Procedure

The dissolution apparatus was set as per parameters. Pellets equivalent to 200 mg of Diprophylline was added in each dissolution vessel and the dissolution test was carried out.

Acceptance Criteria for Ethanol Resistant Formulation

When at least one of the two acceptance criteria (Definition 1 ("plus or minus 20% definition) or Definition 2 (Lower active ingredient release in media with ethanol")) as disclosed in the description was met, the formulation was regarded as ethanol resistant.

Formulation Details
List of Excipients Used in Examples

| S. No. | Name of excipient | Manufacturer/Supplier | Specification |
|---|---|---|---|
| 1. | Metoprolol succinate | Polydrugs, India | USP |
| 2. | Theophylline anhydrous | Aarti Drugs Ltd., India | IP |
| 3. | Tramadol hydrochloride | Aarti Drugs Ltd., India | BP, USP, EP |
| 4. | Diprophylline pellets | NBS Biologicals Ltd., UK | — |
| 5. | Avicel ® PH 101 | FMC biopolymer | USP/NF |
| 6. | Microcrystalline cellulose CL 611 (Viavapur ® MCG 611P) | JRS pharma, Germany | USP/NF |
| 7. | EUDRAGIT ® NE 30 D | Evonik Industries, Germany | Ph. Eur, USP/NF |
| 8. | EUDRAGIT ® NM 30 D | Evonik Industries, Germany | Ph. Eur |

-continued

| S. No. | Name of excipient | Manufacturer/Supplier | Specification |
|---|---|---|---|
| 9. | EUDRAGIT ® L 30D-55 | Evonik Industries, Germany | Ph. Eur, NF |
| 10. | Talc, Luzenac pharma | Imerys, Italy | USP, EP, JP |
| 11. | Guar gum High viscosity (4219 cps) | Merck, India | — |
| 12. | Guar gum Medium viscosity (2000 cps) (Prepared by heating guar gum of 4219 cps) | Merck, India | — |
| 13. | Guar gum Medium viscosity (1000 cps) | Poygal AG, Switzerland | Ph. Eur |
| 14. | Guar gum Low Viscosity cps (150 cps) | Poygal AG, Switzerland | Ph. Eur |
| 15. | Yellow Iron oxide | Standarcon, India | E number -E172 |
| 16. | Methyl paraben | Merck, India | — |
| 17. | Propyl paraben | Merck, India | — |
| 18. | Sugar spheres | Werner, Germany | USP/NF, EP |

Preparation of Pellets for Coating Trials

1. Preparation of Metoprolol Succinate Pellets (16/20#)
Batch Size: 2000 g

| Sr. no. | Ingredients | % w/w | Required quantity (g) |
|---|---|---|---|
| 1. | Metoprolol succinate | 50 | 750 |
| 2. | Avicel PH 101 | 20 | 300 |
| 3. | Microcrystalline cellulose CL 611 | 30 | 450 |
| 4. | Water | | 750 |

Procedure:

1) Metoprolol succinate, Avicel PH 101 and Microcrystalline cellulose CL 611 were sifted through 40# sieve and mixed for 30 min in RMG at slow speed
2) Water 750 g was added to step 1 in RMG under continuous mixing at slow speed, total water added in 3 min. The wet mass was mixed in RMG at slow speed for 2 min with chopper started for 2 min at slow speed.
3) Granulated mass from step 2 was taken for extrusion and desired extrudes were obtained.

Extrusion Parameters:

| | |
|---|---|
| Extrusion type: Axial | Extruder screw: Single |
| Type of screw rotation: Counter clockwise | Screw speed: 50 rpm |
| Screen Diameter: 1 mm | Extrusion pressure: 2.3 bar |
| Feed rate: Manual | |

4) Approximately 350-400 g load was added on spheronization plate (Cross-Hatched type) for spheronization.
5) The extrudates were spheronised at 1700 rpm for 4.0 min to get pellets of optimum size and shape.
6) Resulting pellets were dried at 60° C. for about 2 hours in GPCG 3.1 or 10 hours at 50° C. in tray dryer, till LOD of pellets reached between 1-3%

2. Preparation of Theophylline pellets (16/20#) Batch Size: 2000 g

| Sr. no. | Ingredients | % w/w | Required quantity (g) |
|---|---|---|---|
| 1. | Theophylline | 50 | 1000 |
| 2. | Avicel ® PH 101 | 20 | 400 |
| 3. | Microcrystalline cellulose CL 611 | 30 | 600 |
| 4. | Water | | 1200 |

Procedure:

1) Theophylline, Avicel PH 101 and Microcrystalline cellulose CL 611 were sifted through 40# sieve and mixed for 15 min in RMG at slow speed
2) Water 1200 g was added to step 1 in RMG under continuous mixing at slow speed, total water added in 2 min. The wet mass was mixed in RMG at medium speed for 3 min.
3) Granulated mass from step 2 was taken for extrusion and desired extrudes were obtained.

Extrusion Parameters:

| | |
|---|---|
| Extrusion type: Radial | Extruder screw: Single |
| Type of screw rotation: Counter clockwise | Screw speed: 50 rpm |
| Screen Diameter: 1.0 mm | Extrusion pressure: 2.6 bar |
| Feed rate: Manual | |

4) Approximately 350-400 g load was added on spheronization plate (Cross-Hatched type) for spheronization.
5) The extrudates were spheronised at 1800 rpm for 3 min to get pellets of optimum size and shape.
6) Resulting pellets were dried at 60° C. in GPCG 3.1 till LOD of pellets is between 1-3%

3. Preparation of Tramadol Drug Loaded Pellets
Formula for 25% Drug Loading on 400 g 18/20# Sugar Spheres

| Sr. no. | Ingredients | % w/w | Required quantity (g) |
|---|---|---|---|
| 1. | Sugar spheres | 77.66 | 400 |
| 2. | Tramadol hydrochloride | 19.41 | 100 |
| 3. | Poly vinyl pyrolidine K 30 | 2.91 | 15 |
| 4. | Water | | 460 |

Procedure:

1) Tramadol hydrochloride was dissolved in water under stirring for 10 minutes using overhead stirrer.
2) PVP K30 was then added to the Tramadol HCl solution and stirred for 20 minutes. Prepared solution of drug and binder was taken for drug loading onto sugar spheres.
3) Drug loading was carried out using Pam Glatt GPCG 1.1 fluid bed processer.

Coating Parameters:

| Parameters | Unit | Value |
|---|---|---|
| Batch size | g | 400 |
| Nozzle | mm | 0.8 |
| Air flow | cfm | 58-62 |
| Atomization pressure | bar | 08-1.0 |

| Parameters | Unit | Value |
|---|---|---|
| Spray rate | g/min | 1.0.-3.5 |
| Inlet air temperature | ° C. | 37-50 |
| Product temperature | ° C. | 32-42 |

4. Preparation of Diprophylline Pellets

Pellets readily available from NBS Biologicals Ltd., UK
Examples for Monolayer Composition Example 1C (Comparative)

Trial with EUDRAGIT NE30 D alone
Core used: Theophylline pellets (16/20#)
Batch size: 80 g
Formulation Details:
Formula for 15% EUDRAGIT® NE 30D coating on 80 g pellets

|  | % on polymer | Solids (g) | Quantity taken (g) |
|---|---|---|---|
| EUDRAGIT ® NE 30 D |  | 12.0 | 40.0 |
| Talc | 50.00 | 6.0 | 6.0 |
| Water |  |  | 74.0 |
| Total |  | 18.0 | 120.0 |

Solid content of coating dispersion=15% w/w
Procedure:
1. Talc was homogenized in water for 20 min.
2. EUDRAGIT® NE30D and Talc dispersion were then mixed for 15 min.
3. Coating dispersion was filtered through 60# sieve and used for coating.
4. Coating was carried out using Mycrolab Huttlin fluid bed processor.
5. Coating up to 15% of EUDRAGIT® NE 30D was done.
6. Pellets were cured for 24 hours at 50° C. in tray dryer.

Coating Parameters:

| Parameters | Unit | Value |
|---|---|---|
| Batch size | g | 80 |
| Nozzle | mm | 0.6 |
| Air flow | m³/h | 25-29 |
| Atomization pressure | bar | 1.0 |
| Spray rate | g/min | 0.5-2.5 |
| Inlet air temperature | ° C. | 27-31 |
| Product temperature | ° C. | 25-26 |

Results and Discussion:

| Media | Time (min.) | 0.1N HCl-buffer pH 6.8 % Release | 40% Alcoholic 0.1N HCl-buffer pH 6.8 % Release | Deviation in Absolute % |
|---|---|---|---|---|
| Acid | 0 | 0.0 | 0.0 | 0.0 |
| Stage (pH 1.2) | 30 | 0.0 | 0.9 | +0.9 |
|  | 60 | 0.0 | 2.3 | +2.3 |
|  | 90 | 0.0 | 5.0 | +5.0 |
|  | 120 | 0.0 | 27.5 | +27.5 |
| Buffer stage (pH 6.8) | 240 | 0.0 | 82.8 | +82.8 |
|  | 480 | 0.2 | 89.4 | +89.2 |
|  | 720 | 0.4 | 91.7 | +91.3 |

Release profile in Ethanolic medium is higher than non-Ethanolic medium. This release profile appears/considered to be not following either Definition 1 ("plus or minus 20% definition) or Definition 2 (Lower active ingredient release in media with ethanol"). Thus, Example 1C (EUDRAGIT® NE30D coated pellets) failed to give alcohol resistance.

Example 2 (Inventive Example)

Trial with EUDRAGIT® NE30D: Guar gum High viscosity in 90:10 ratio
Core used: Metoprolol succinate pellets (16/20#)
Batch size: 400 g
Formulation Details:
Formula for 15% EUDRAGIT® NE 30D coating on 400 g pellets

|  | Ratio | % on polymer | Solids(g) | Quantity (g) |
|---|---|---|---|---|
| EUDRAGIT ® NE 30 D | 90 |  | 60.0 | 200 |
| Guar Gum High viscosity (4219 cps) | 10 | 11.11 | 6.67 | 6.67 |
| Talc |  | 50.00 | 30.0 | 30.0 |
| Yellow Iron Oxide |  | 0.50 | 0.3 | 0.3 |
| Water |  |  |  | 1702.31 |
|  |  |  | 96.97 | 1939.27 |

Solid content of coating dispersion=5% w/w
Procedure:
1. Talc and yellow iron oxide was homogenized in water for 20 min.
2. Guar gum was dissolved in water under overhead stirring for 30 min.
3. EUDRAGIT® NE30D and Talc dispersion were then added to the Guar gum solution and mixed for 15 min.
4. Coating dispersion was filtered through 60# sieve and used for coating.
5. Coating was carried out using Pam Glatt 1.1 fluid bed processor.
6. Coating up to 15% of EUDRAGIT® NE30D was done.
7. Pellets were cured for 24 hours at 50° C. in tray dryer.

Coating Parameters:

| Parameters | Unit | Value |
|---|---|---|
| Batch size | g | 400 |
| Nozzle | mm | 0.8 |
| Air flow | cfm | 85-88 |
| Atomization pressure | bar | 1.1-1.3 |
| Spray rate | g/min | 0.8-9.6 |
| Inlet air temperature | ° C. | 27-40 |
| Product temperature | ° C. | 26-29 |

Results and Discussion:

| Media | Time in mins. | 0.1N HCl % Release | 40% EtOH 0.1N HCl % Release | Deviation in Absolute % |
|---|---|---|---|---|
| Acid | 0 | 0.0 | 0.0 | 0.0 |
| Stage | 30 | 11.3 | 7.9 | −3.4 |
| (pH 1.2) | 60 | 80.8 | 33.1 | −47.7 |
| | 90 | 99.7 | 58.0 | −41.7 |
| | 120 | 101.4 | 75.5 | −25.9 |

The release profile in the ethanolic medium is lower than non-ethanolic medium (Definition 2) is fulfilled. The deviations are partially more than −20% (Definition 1 is not fulfilled). Thus, composition of Example 2 is considered to be Ethanol resistant because of matching with Definition 2.

Example 3 (Inventive Example)

Trial with EUDRAGIT® NE30D: Guar gum High viscosity in 93:7 ratio without preservative and pigment
Core used: Metoprolol succinate pellets (16/20#)
Batch size: 400 g
Formulation Details:
Formula for 40% EUDRAGIT NE 30D coating on 400 g pellets

| | Ratio | % on polymer | Solids(g) | Quantity (g) |
|---|---|---|---|---|
| EUDRAGIT® NE 30 D | 93 | | 160.0 | 533.32 |
| Guar Gum High viscosity (4219 cps) | 7 | 7.53 | 12.04 | 6.67 |
| Talc | | 50.00 | 80.0 | 80 |
| Water | | | | 3575.34 |
| Total | | | 252.04 | 4200.71 |

Solid content of coating dispersion=6% w/w
Procedure:
1. Talc was homogenized in 400 g of water for 20 min.
2. Guar gum was dissolved in remaining water under overhead stirring for 30 min.
3. EUDRAGIT® NE30D and Talc dispersion were then added to the Guar gum solution and mixed for 15 min.
4. Coating dispersion was filtered through 60# sieve and used for coating.
5. Coating was carried out using Glatt 1.1 fluid bed processor.
6. Coating up to 40% of EUDRAGIT® NE30D was done.
7. Pellets were cured for 24 hours at 50° C. in tray dryer.
Coating Parameters:

| Parameters | Unit | Value |
|---|---|---|
| Batch size | g | 400 |
| Nozzle | mm | 0.8 |
| Air flow | m³/h | 160-215 |
| Atomization pressure | bar | 1.1-1.3 |
| Spray rate | g/min | 1.0-12 |
| Inlet air temperature | ° C. | 28-40 |
| Product temperature | ° C. | 27-29 |

Results and Discussion:

| Media | Time in mins. | 0.1N HCl-buffer pH 6.8 % Release | 40% Alcoholic 0.1N HCl-buffer pH 6.8 % Release | Deviation in Absolute % |
|---|---|---|---|---|
| Acid | 0 | 0.0 | 0.0 | 0.0 |
| Stage | 15 | 0.0 | 0.0 | 0.0 |
| (pH 1.2) | 30 | 0.0 | 1.1 | +1.1 |
| | 60 | 1.0 | 2.3 | +1.3 |
| | 90 | 3.4 | 5.6 | +2.2 |
| | 120 | 9.2 | 12.1 | +2.9 |
| Buffer | 240 | 66.4 | 62.5 | −3.9 |
| stage | 480 | 99.0 | 97.5 | −1.5 |
| (pH 6.8) | 720 | 101.4 | 102.1 | +0.7 |

The release profile in the ethanolic medium is as per Definition 1 ("plus or minus 20% definition"). Thus, composition of Example 3 is considered to be Ethanol resistant because of matching with Definition 1.

Example 4 (Inventive Example)

Trial with EUDRAGIT® NE30D: Guar gum High viscosity in 93:7 ratio
Core used: Metoprolol succinate pellets (16/20#)
Batch size: 400 g
Formulation Details:
Formula for 40% EUDRAGIT® NE 30D coating on 400 g pellets

| | Ratio | % on polymer | Solids(g) | Quantity(g) |
|---|---|---|---|---|
| EUDRAGIT® NE 30 D | 93 | | 160.0 | 533.34 |
| Guar Gum High viscosity 4219 cps | 7 | 7.53 | 12.04 | 12.04 |
| Talc | | 50.00 | 80.0 | 80.0 |
| Yellow Iron Oxide | | 0.50 | 0.80 | 0.80 |
| Methyl paraben | | 0.18% on guar gum | 0.021 | 0.021 |
| Propyl paraben | | 0.09% on guar gum | 0.010 | 0.010 |
| Water | | | | 3702 |
| Total | | | 252.87 | 4326.17 |

Solid content of coating dispersion=5.84% w/w
Procedure:
1. Talc and yellow iron oxide was homogenized in water for 20 min.
2. Methyl paraben and Guar gum was dissolved in water under overhead stirring for 30 min.
3. Propyl paraben was dissolved in small quantity of hot water (50° C.) and then added to guar gum dispersion.
4. EUDRAGIT® NE30D and Talc dispersion were then added to the Guar gum solution and mixed for 15 min.
5. Coating dispersion was filtered through 60# sieve and used for coating.
6. Coating was carried out using Glatt 1.1 fluid bed processor.
7. Coating up to 40% of EUDRAGIT® NE30D was done.
8. Pellets were cured for 24 hours at 50° C. in tray dryer.
Coating Parameters:

| Parameters | Unit | Value |
|---|---|---|
| Batch size | g | 400 |
| Nozzle | mm | 0.8 |
| Air flow | m³/h | 160-190 |

-continued

| Parameters | Unit | Value |
| --- | --- | --- |
| Atomization pressure | bar | 1.0-1.2 |
| Spray rate | g/min | 1.6-10.5 |
| Inlet air temperature | ° C. | 29-35 |
| Product temperature | ° C. | 26-28 |

Results and Discussion:

| Media | Time in mins. | 0.1N HCl-buffer pH 6.8 % Release | 40% Alcoholic 0.1N HCl-buffer pH 6.8 % Release | Deviation in Absolute % |
| --- | --- | --- | --- | --- |
| Acid | 0 | 0.0 | 0.0 | 0.0 |
| Stage | 60 | 4.3 | 2.8 | −1.5 |
| (pH 1.2) | 120 | 42.3 | 23.4 | −18.9 |
| Buffer | 240 | 89.3 | 82.1 | −7.2 |
| stage | 480 | 92.4 | 94.9 | +2.5 |
| (pH 6.8) | 720 | 92.6 | 95.8 | +3.2 |

The release profile in the Ethanolic medium is as per Definition 1 ("plus or minus 20% definition"). Thus, composition of Example 4 is considered to be Ethanol resistant because of matching with Definition 1.

Example 5 (Inventive Example)

Trial with EUDRAGIT® NE30D: Guar gum medium viscosity in 93:7 ratio
Core used: Metoprolol succinate pellets (16/20#)
Batch size: 400 g
Formulation Details:
Formula for 40% EUDRAGIT® NE 30D coating on 400 g pellets

| | Ratio | % on polymer | Solids(g) | Quantity(g) |
| --- | --- | --- | --- | --- |
| EUDRAGIT ® NE 30 D | 93 | | 160.0 | 533.34 |
| Guar Gum medium viscosity (1000 cps) | 7 | 7.53 | 12.04 | 12.04 |
| Talc | | 50.00 | 80.0 | 80.0 |
| Yellow Iron Oxide | | 0.50 | 0.80 | 0.80 |
| Methyl paraben | | 0.18% on guar gum | 0.021 | 0.021 |
| Propyl paraben | | 0.09% on guar gum | 0.010 | 0.010 |
| Water | | | | 1481.09 |
| Total | | | 252.87 | 2107.29 |

Solid content of coating dispersion=12% w/w
Procedure:
1. Yellow iron oxide was homogenized in water for 20 min.
2. Guar gum, Talc, Methyl paraben and Propyl paraben was dissolved in water under overhead stirring for 30 min.
3. Yellow iron oxide dispersion and EUDRAGIT® NE 30D was then added into step 2 dispersion under stirring and mixed for 15 min.
4. Coating dispersion was filtered through 60# sieve and used for coating.
5. Coating was carried out using Pam Glatt 1.1 fluid bed processor.
6. Coating up to 40% of EUDRAGIT® NE 30D was done.
7. Pellets were cured for 24 hours at 50° C. in tray dryer.

Coating Parameters:

| Parameters | Unit | Value |
| --- | --- | --- |
| Batch size | g | 400 |
| Nozzle | mm | 0.8 |
| Air flow | cfm | 81-85 |
| Atomization pressure | bar | 1.1-1.3 |
| Spray rate | g/min | 2-10 |
| Inlet air temperature | ° C. | 30-36 |
| Product temperature | ° C. | 27-28 |

Results and Discussion:

| Media | Time in mins. | 0.1N HCl - buffer pH 6.8 % Release | 40% Alcoholic 0.1N HCl - buffer pH 6.8 % Release | Deviation in Absolute % |
| --- | --- | --- | --- | --- |
| Acid stage | 0 | 0.0 | 0.0 | 0.0 |
| | 60 | 12.8 | 5.4 | −7.4 |
| | 120 | 77.2 | 25.9 | −51.3 |
| Buffer stage | 240 | 96.8 | 88.2 | −8.6 |
| | 480 | 97.2 | 96.2 | −1.0 |

The release profile in the ethanolic medium is lower than the non-ethanolic medium (Definition 2) is fulfilled. The deviations are more than −20% (Definition 1 is not fulfilled). Thus, composition of Example 5 is considered to be Ethanol resistant because of matching with Definition 2.

Example 6 (Inventive Example)

Trial with EUDRAGIT® NE30D: Guar gum low viscosity in 93:7 ratio
Core used: Metoprolol succinate pellets (16/20#)
Batch size: 400 g
Formulation Details:
Formula for 40% EUDRAGIT® NE 30D coating on 400 g pellets

| | Ratio | % on polymer | Solids(g) | Quantity(g) |
| --- | --- | --- | --- | --- |
| EUDRAGIT ® NE 30 D | 93 | | 160.0 | 533.34 |
| Guar Gum low viscosity (150 cps) | 7 | 7.53 | 12.04 | 12.04 |
| Talc | | 50.00 | 80.0 | 80.0 |
| Yellow Iron Oxide | | 0.50 | 0.80 | 0.80 |
| Methyl paraben | | 0.18% on guar gum | 0.021 | 0.021 |
| Propyl paraben | | 0.09% on guar gum | 0.010 | 0.010 |
| Water | | | | 1059.63 |
| Total | | | 252.87 | 1685.83 |

Solid content of dispersion=15% w/w
Procedure:
1. Yellow iron oxide was homogenized in water for 20 min.
2. Guar gum, Talc, Methyl paraben and Propyl paraben was dissolved in water under overhead stirring for 30 min.
3. Yellow iron oxide dispersion and EUDRAGIT® NE 30D was then added in to step 2 dispersion under stirring and mixed for 15 min.

4. Coating dispersion was filtered through 60# sieve and used for coating.
5. Coating was carried out using Pam Glatt 1.1 fluid bed processor.
6. Coating up to 40% of EUDRAGIT® NE30D was done.
7. Pellets were cured for 24 hours at 50° C. in tray dryer.

Coating Parameters:

| Parameters | Unit | Value |
| --- | --- | --- |
| Batch size | g | 400 |
| Nozzle | mm | 0.8 |
| Air flow | cfm | 78-88 |
| Atomization pressure | bar | 1.1-1.3 |
| Spray rate | g/min | 1.5-10 |
| Inlet air temperature | ° C. | 30-36 |
| Product temperature | ° C. | 27-28 |

Results and Discussion:

| Media | Time in mins. | 0.1N HCl - buffer pH 6.8 % Release | 40% Alcoholic 0.1N HCl - buffer pH 6.8 % Release | Deviation in Absolute % |
| --- | --- | --- | --- | --- |
| Acid stage | 0 | 0.0 | 0.0 | 0.0 |
|  | 60 | 2.5 | 2.9 | +0.4 |
|  | 120 | 27.3 | 19.8 | -7.5 |
| Buffer stage | 240 | 87.0 | 74.5 | -12.5 |
|  | 480 | 98.2 | 94.5 | -3.7 |
|  | 720 | 99.3 | 97.9 | -1.4 |

The release profile in the Ethanolic medium is as per Definition 1 ("plus or minus 20% definition"). Thus, composition of Example 6 is considered to be Ethanol resistant because of matching with Definition 1.

Example 7 (Inventive Example)

Trial with EUDRAGIT® NM 30D: Guar gum medium viscosity in 93:7 ratio
Core used: Metoprolol succinate pellets (16/20#)
Batch size: 400 g
Formulation Details:
Formula for 40% EUDRAGIT® NM 30D coating on 400 g pellets

|  | Ratio | % on polymer | Solids(g) | Quantity(g) |
| --- | --- | --- | --- | --- |
| EUDRAGIT ® NM 30 D | 93 |  | 160.0 | 533.34 |
| Guar Gum medium viscosity (1000 cps) | 7 | 7.53 | 12.04 | 12.04 |
| Talc |  | 50.00 | 80.0 | 80.0 |
| Yellow Iron Oxide |  | 0.50 | 0.80 | 0.80 |
| Methyl paraben |  | 0.18% on guar gum | 0.021 | 0.021 |
| Propyl paraben |  | 0.09% on guar gum | 0.010 | 0.010 |
| Water |  |  |  | 1481.09 |
| Total |  |  | 252.87 | 2107.29 |

Solid content of coating dispersion=12% w/w
Procedure:
1. Yellow iron oxide was homogenized in water for 20 min.
2. Guar gum, Talc, Methyl paraben and Propyl paraben was dissolved in water under overhead stirring for 30 min.
3. Yellow iron oxide dispersion and EUDRAGIT® NM 30D was then added in to step 2 dispersion under stirring and mixed for 15 min.
4. Coating dispersion was filtered through 60# sieve and used for coating.
5. Coating was carried out using Pam Glatt 1.1 fluid bed processor.
6. Coating up to 40% of EUDRAGIT® NM 30D was done.
7. Pellets were cured for 24 hours at 50° C. in tray dryer.

Coating Parameters:

| Parameters | Unit | Value |
| --- | --- | --- |
| Batch size | g | 400 |
| Nozzle | mm | 0.8 |
| Air flow | cfm | 79-83 |
| Atomization pressure | bar | 1.1-1.3 |
| Spray rate | g/min | 2-11 |
| Inlet air temperature | ° C. | 30-38 |
| Product temperature | ° C. | 27-28 |

Results and Discussion:

| Media | Time in mins. | 0.1N HCl - buffer pH 6.8 % Release | 40% Alcoholic 0.1N HCl - buffer pH 6.8 % Release | Deviation in Absolute % |
| --- | --- | --- | --- | --- |
| Acid stage | 0 | 0.0 | 0.0 | 0.0 |
|  | 60 | 2.1 | 0.8 | -1.3 |
|  | 120 | 24.8 | 2.3 | -22.5 |
| Buffer stage | 240 | 84.0 | 15.7 | -68.3 |
|  | 480 | 94.9 | 86.8 | -8.1 |

The release profile in the ethanolic medium is lower than the non-ethanolic medium (Definition 2) is fulfilled. The deviations are more than −20% (Definition 1 is not fulfilled). Thus, composition of Example 7 is considered to be Ethanol resistant because of matching with Definition 2.

Example 8 (Inventive Example)

Trial with EUDRAGIT® NE 30D: Guar gum in 95:5 ratio
Core used: Metoprolol succinate pellets (16/20#)
Batch size: 400 g
Formulation Details:
Formula for 40% EUDRAGIT® NE 30D on 400 g pellets

|  | Ratio | % on polymer | Solids(g) | Quantity(g) |
| --- | --- | --- | --- | --- |
| EUDRAGIT ® NE 30 D | 95 |  | 160.0 | 534 |
| Guar Gum High viscosity 4219 cps | 5 | 5.26 | 8.42 | 8.42 |
| Talc |  | 50.00 | 80.0 | 80.0 |
| Yellow Iron Oxide |  | 0.50 | 0.8 | 0.8 |
| Methyl paraben |  | 0.18% on guar gum | 0.015 | 0.015 |
| Propyl paraben |  | 0.09% on guar gum | 0.007 | 0.007 |
| Water |  |  |  | 1869.66 |
| Total |  |  | 249.24 | 2492.90 |

Solid content of dispersion=10% w/w
Procedure:
1. Talc and yellow iron oxide was homogenized in water for 20 min.

2. Methyl paraben and Guar gum was dissolved in water under overhead stirring for 30 min.
3. Propyl paraben was dissolved in small quantity of hot water (50° C.) and then added to guar gum dispersion.
4. EUDRAGIT® NE30D and Talc dispersion were then added to the Guar gum solution and mixed for 15 min.
5. Coating dispersion was filtered through 60# sieve and used for coating.
6. Coating was carried out using Glatt 1.1 fluid bed processor.
7. Coating up to 40% of NE30D was done.
8. Pellets were cured for 24 hours at 50° C. in tray dryer.

Coating Parameters:

| Parameters | Unit | Value |
| --- | --- | --- |
| Batch size | g | 400 |
| Nozzle | mm | 0.8 |
| Air flow | m³/h | 190-200 |
| Atomization pressure | bar | 1.1-1.2 |
| Spray rate | g/min | 1.0-12 |
| Inlet air temperature | ° C. | 26-36 |
| Product temperature | ° C. | 26-27 |

Results and Discussion:

| Media | Time in mins. | 0.1N HCl - buffer pH 6.8 % Release | 40% Alcoholic 0.1N HCl - buffer pH 6.8 % Release | Deviation in Absolute % |
| --- | --- | --- | --- | --- |
| Acid stage | 0 | 0.0 | 0.0 | 0.0 |
| | 15 | 0.0 | 0.0 | 0.0 |
| | 30 | 0.0 | 0.0 | 0.0 |
| | 60 | 0.5 | 1.1 | +0.6 |
| | 90 | 1.4 | 2.9 | +1.5 |
| | 120 | 3.2 | 10.1 | +6.9 |
| Buffer stage | 240 | 36.4 | 47.8 | +11.4 |
| | 480 | 93.5 | 79.4 | −14.1 |
| | 720 | 98.6 | 87.1 | −11.5 |

The release profile in the Ethanolic medium is as per Definition 1 ("plus or minus 20% definition"). Thus, composition of Example 8 is considered to be Ethanol resistant because of matching with Definition 1.

Example 9 C (Comparative example)

Trial with EUDRAGIT® NE 30D: Guar gum in 97:3 ratio
Core used: Metoprolol succinate pellets (16/20#)
Formulation Details:
Formula for 15% EUDRAGIT® NE 30 D coating on 400 g pellets

| | Ratio | % on polymer | Solid(g) | Quantity(g) |
| --- | --- | --- | --- | --- |
| EUDRAGIT® NE 30 D | 97 | | 60 | 199.99 |
| Guar Gum High viscosity 4219 cps | 3 | 3.09 | 1.86 | 1.86 |
| Talc | | 50.00 | 30 | 30 |
| Yellow Iron Oxide | | 0.50 | 0.3 | 0.3 |
| Methyl paraben | | 0.18% on guar gum | 0.003 | 0.003 |
| Propyl paraben | | 0.09% on guar gum | 0.002 | 0.002 |
| Water | | | | 535.84 |
| Total | | | 92.16 | 768.0 |

Solid content or dispersion=12% w/w
Procedure:
1. Talc and yellow iron oxide was homogenized in water for 20 min.
2. Methyl paraben and Guar gum was dissolved in water under overhead stirring for 30 min.
3. Propyl paraben was dissolved in small quantity of hot water (50° C.) and then added to guar gum dispersion.
4. EUDRAGIT® NE30D and Talc dispersion were then added to the Guar gum solution and mixed for 15 min.
5. Coating dispersion was filtered through 60# sieve and used for coating.
6. Coating was carried out using Pam Glatt 1.1 fluid bed processor.
7. Coating up to 15% of EUDRAGIT® NE 30D was done.
8. Pellets were cured for 24 hours at 50° C. in tray dryer.

Coating Parameters:

| Parameters | Unit | Value |
| --- | --- | --- |
| Batch size | g | 400 |
| Nozzle | mm | 0.8 |
| Air flow | cfm | 86-93 |
| Atomization pressure | bar | 1.0-1.1 |
| Spray rate | g/min | 1.5-8.0 |
| Inlet air temperature | ° C. | 27-36 |
| Product temperature | ° C. | 25-28 |

Results and Discussion:

| Media | Time in mins. | 0.1N HCl % Release | 40% Alco. 0.1N HCl % Release | Deviation in Absolute % |
| --- | --- | --- | --- | --- |
| Acid stage | 0 | 0.0 | 0.0 | 0.0 |
| | 15 | 0.0 | 1.0 | +1.0 |
| | 30 | 0.0 | 3.6 | +3.6 |
| | 60 | 0.6 | 21.3 | +20.7 |
| | 90 | 1.3 | 42.9 | +41.6 |
| | 120 | 2.7 | 60.1 | +57.4 |

Release profile in Ethanolic medium is higher than non-Ethanolic medium. This release profile appears/considered to be not following either Definition 1 ("plus or minus 20% definition") or definition 2 (Lower active ingredient release in media with ethanol"). Thus, Example 9C (EUDRAGIT® NE 30D: Guar gum in 97:3 ratio) failed to give alcohol resistance.

Example 10 (Inventive Example)

Trial with EUDRAGIT® NE 30D: Guar gum in 93:7 ratio
Core used: Theophylline pellets (16/20#)
Formulation Details:
Batch size: 400 g
Formula for 30% EUDRAGIT® NE30D coating on 400 g pellets

| | Ratio | % on polymer | Solids(g) | Quantity(g) |
|---|---|---|---|---|
| EUDRAGIT® NE 30 D | 93 | | 120 | 400.0 |
| Guar Gum High viscosity 4219 cps | 7 | 7.53 | 9.03 | 9.03 |
| Talc | | 50.00 | 60 | 60 |
| Yellow Iron Oxide | | 0.50 | 0.6 | 0.6 |
| Methyl paraben | | 0.18% on guar gum | 0.016 | 0.016 |
| Propyl paraben | | 0.09% on guar gum | 0.008 | 0.008 |
| Water | | | | 2691.29 |
| | | | 189.65 | 3160.94 |

Solid content of dispersion=6% w/w

Procedure:

1. Talc and yellow iron oxide was homogenized in water for 20 min.
2. Methyl paraben and Guar gum was dissolved in water under overhead stirring for 30 min.
3. Propyl paraben was dissolved in small quantity of hot water (50° C.) and then added to guar gum dispersion.
4. EUDRAGIT® NE30D and Talc dispersion were then added to the Guar gum solution mixed for 15 min.
5. Coating dispersion was filtered through 60# sieve and used for coating.
6. Coating was carried out using Glatt 1.1 fluid bed processor.
7. Coating up to 30% of NE30D was done.
8. Pellets were cured for 24 hours at 50° C. in tray dryer.

Coating Parameters:

| Parameters | Unit | Value |
|---|---|---|
| Batch size | g | 400 |
| Nozzle | mm | 0.8 |
| Air flow | m³/h | 150-190 |
| Atomization pressure | bar | 1.1-1.3 |
| Spray rate | g/min | 1-12 |
| Inlet air temperature | ° C. | 30-39 |
| Product temperature | ° C. | 28-29 |

Results and Discussion:

| Media | Time in mins. | 0.1N HCl - buffer pH 6.8 % Release | 40% Alcoholic 0.1N HCl - buffer pH 6.8 % Release | Deviation in Absolute % |
|---|---|---|---|---|
| Acid stage | 0 | 0.0 | 0.0 | 0.0 |
| | 60 | 1.0 | 2.2 | +1.1 |
| | 120 | 4.9 | 7.0 | +2.1 |
| Buffer stage | 240 | 15.4 | 14.1 | −1.3 |
| | 480 | 52.5 | 36.1 | −16.4 |
| | 720 | 84.8 | 67.4 | −17.4 |

The release profile in the Ethanolic medium is as per Definition 1 ("plus or minus 20% definition"). Thus, composition of Example 10 is considered to be Ethanol resistant because of matching with Definition 1.

Example 11 (Inventive Example)

Trial with EUDRAGIT® NE30D: Guar gum medium viscosity in 93:7 ratio

Core used: Tramadol hydrochloride drug loaded pellets (16/20#)

Batch size: 400 g

Formulation Details:

Formula for 40% EUDRAGIT® NE 30D coating on 400 g pellets

| | Ratio | % on polymer | Solids(g) | Quantity(g) |
|---|---|---|---|---|
| EUDRAGIT® NE 30 D | 93 | | 160.0 | 533.34 |
| Guar Gum medium viscosity (1000 cps) | 7 | 7.53 | 12.04 | 12.04 |
| Talc | | 50.00 | 80.0 | 80.0 |
| Yellow Iron Oxide | | 0.50 | 0.80 | 0.80 |
| Methyl paraben | | 0.18% on guar gum | 0.021 | 0.021 |
| Propyl paraben | | 0.09% on guar gum | 0.010 | 0.010 |
| Water | | | | 1481.09 |
| Total | | | 252.87 | 2107.29 |

Solid content of dispersion=12% w/w

Procedure:

1. Yellow iron oxide was homogenized in water for 20 min.
2. Guar gum, Talc, Methyl paraben and Propyl paraben was dissolved in water under overhead stirring for 30 min.
3. Yellow iron oxide dispersion and EUDRAGIT® NE 30D was then added in to step 2 dispersion under stirring and mixed for 15 min.
4. Coating dispersion was filtered through 60# sieve and used for coating.
5. Coating was carried out using Pam Glatt 1.1 fluid bed processor.
6. Coating up to 40% of EUDRAGIT® NE 30D was done.
7. Pellets were cured for 24 hours at 50° C. in tray dryer.

Coating Parameters:

| Parameters | Unit | Value |
|---|---|---|
| Batch size | g | 400 |
| Nozzle | mm | 0.8 |
| Air flow | cfm | 80-90 |
| Atomization pressure | bar | 1.0-1.3 |
| Spray rate | g/min | 1-10 |
| Inlet air temperature | ° C. | 30-50 |
| Product temperature | ° C. | 27-42 |

Results and Discussion:

| Media | Time in mins. | 0.1N HCl - buffer pH 6.8 % Release | 40% Alcoholic 0.1N HCl - buffer pH 6.8 % Release | Deviation in Absolute % |
|---|---|---|---|---|
| Acid stage | 0 | 0.0 | 0.0 | 0.0 |
| | 60 | 12.2 | 7.7 | −4.5 |
| | 120 | 90.1 | 31.6 | −58.5 |

| Media | Time in mins. | 0.1N HCl - buffer pH 6.8 % Release | 40% Alcoholic 0.1N HCl - buffer pH 6.8 % Release | Deviation in Absolute % |
|---|---|---|---|---|
| Buffer stage | 240 | 95.5 | 92.0 | −3.5 |
| | 480 | 96.8 | 96.7 | −0.1 |
| | 720 | 96.8 | 94.3 | −2.5 |

The release profile in the ethanolic medium is lower than in the non-ethanolic medium (Definition 2) is fulfilled. Thus, composition of Example 11 is considered to be Ethanol resistant because of matching with Definition 2.

Example 12 (Inventive Example)

Trial with EUDRAGIT® NE30D: Guar gum medium viscosity in 93:7 ratio
Core used: Diprophylline drug loaded pellets (18/20#)
Batch size: 400 g
Formulation Details:
Formula for 30% EUDRAGIT® NM 30D coating on 400 g pellets

| | Ratio | % on polymer | Solids (g) | Quantity (g) |
|---|---|---|---|---|
| EUDRAGIT® NM 30 D | 93 | | 120.0 | 400.0 |
| Guar Gum medium viscosity (1000 cps) | 7 | 7.53 | 9.03 | 9.03 |
| Talc | | 50.00 | 60.0 | 60.0 |
| Yellow Iron Oxide | | 0.50 | 0.60 | 0.60 |
| Methyl paraben | | 0.18% on guar gum | 0.016 | 0.016 |
| Propyl paraben | | 0.09% on guar gum | 0.008 | 0.008 |
| Water | | | | 1110.89 |
| Total | | | 189.65 | 1579 |

Solid content of dispersion=12% w/w
Procedure:
1. Yellow iron oxide was homogenized in water for 20 min.
2. Guar gum, Talc, Methyl paraben and Propyl paraben was dissolved in water under overhead stirring for 30 min.
3. Yellow iron oxide dispersion and EUDRAGIT® NM 30D was then added into step 2 dispersion under stirring and mixed for 15 min.
4. Coating dispersion was filtered through 60# sieve and used for coating.
5. Coating was carried out using Pam Glatt 1.1 fluid bed processor.
6. Coating up to 40% of EUDRAGIT® NM 30D was done.
7. Pellets were cured for 24 hours at 50° C. in tray dryer.

Coating Parameters:

| Parameters | Unit | Value |
|---|---|---|
| Batch size | g | 400 |
| Nozzle | mm | 0.8 |
| Air flow | cfm | 84-92 |
| Atomization pressure | bar | 1.2-1.4 |
| Spray rate | g/min | 2-7 |
| Inlet air temperature | ° C. | 30-38 |
| Product temperature | ° C. | 26-28 |

Results and Discussion:

| Media | Time in mins. | 0.1N HCl - buffer pH 6.8 % Release | 40% Alcoholic 0.1N HCl - buffer pH 6.8 % Release | Deviation in Absolute % |
|---|---|---|---|---|
| Acid stage | 0 | 0.0 | 0.0 | 0.0 |
| | 60 | 39.6 | 3.1 | −36.5 |
| | 120 | 99.4 | 15.8 | −83.6 |
| Buffer stage | 240 | — | 90.5 | — |
| | 480 | — | 101.9 | — |
| | 720 | — | 104.3 | — |

The release profile in the ethanolic medium is lower than in the non-ethanolic medium (Definition 2) is fulfilled. Thus, composition of Example 12 is considered to be Ethanol resistant because of matching with Definition 2.

Example 13 (Inventive Example)

Trial with EUDRAGIT® NM 30D: Guar gum medium viscosity in 93:7 ratio with polyethylene glycol as anti-tacking agent
Core used: Metoprolol succinate pellets (16/20#)
Batch size: 400 g
Formulation Details:
Formula for 40% EUDRAGIT® NM 30D coating on 400 g pellets

| | Ratio | % on polymer | Solids (g) | Quantity (g) |
|---|---|---|---|---|
| EUDRAGIT® NM 30 D | 93 | | 160.0 | 533.34 |
| Guar Gum medium viscosity (1000 cps) | 7 | 7.53 | 12.04 | 12.04 |
| Poly Ethylene Glycol (PEG) 20000 | | 5.0 | 8.0 | 8.0 |
| Yellow Iron Oxide | | 0.50 | 0.80 | 0.80 |
| Methyl paraben | | 0.18% on guar gum | 0.021 | 0.021 |
| Propyl paraben | | 0.09% on guar gum | 0.010 | 0.010 |
| Water | | | | 953.09 |
| Total | | | 180.87 | 1507.29 |

Solid content of coating dispersion=12% w/w
Procedure:
1. Yellow iron oxide was homogenized in water for 20 min.
2. Guar gum, PEG 20000, Methyl paraben and Propyl paraben was dissolved in water under overhead stirring for 30 min.
3. Yellow iron oxide dispersion and EUDRAGIT® NM 30D was then added in to step 2 dispersion under stirring and mixed for 15 min.
4. Coating dispersion was filtered through 60# sieve and used for coating.
5. Coating was carried out using Pam Glatt 1.1 fluid bed processor.

6. Coating up to 40% of EUDRAGIT® NM30D was done.
7. Pellets were cured for 24 hours at 50° C. in tray dryer.

Coating Parameters:

| Parameters | Unit | Value |
|---|---|---|
| Batch size | g | 400 |
| Nozzle | mm | 0.8 |
| Air flow | cfm | 90-108 |
| Atomization pressure | bar | 1.1-1.4 |
| Spray rate | g/min | 1-8 |
| Inlet air temperature | ° C. | 28-36 |
| Product temperature | ° C. | 26-28 |

Results and Discussion:

| Media | Time in mins. | 0.1N HCl - buffer pH 6.8 % Release | 40% Alcoholic 0.1N HCl - buffer pH 6.8 % Release | Deviation in Absolute % |
|---|---|---|---|---|
| Acid stage | 0 | 0.0 | 0.0 | 0.0 |
|  | 60 | 5.9 | 2.9 | −3.0 |
|  | 120 | 38.9 | 20.0 | −18.9 |
| Buffer stage | 240 | 80.7 | 67.7 | −13.0 |
|  | 480 | 82.5 | 93.4 | +10.9 |
|  | 720 | 84.3 | 96.3 | +12.0 |

The release profile in the Ethanolic medium is as per Definition 1 ("plus or minus 20% definition). Thus, composition of Example 13 is considered to be Ethanol resistant because of matching with Definition 1.

Examples for Bilayer Composition

Example 14C (Comparative for Bilayer)

Trial with EUDRAGIT® NE 30D +HPC LM (11.5% on EUDRAGIT NE)
Core used: Metoprolol succinate pellets (16/20#)
Batch size: 1000 g
Formulation Details:
Formula for 10% EUDRAGIT® NE 30D coating on 1000 g pellets

|  | % on polymer | Solids (g) | Quantity (g) |
|---|---|---|---|
| EUDRAGIT ® NE 30 D |  | 100 | 333.33 |
| Hydroxy propyl cellulose HPC LM | 11.50 | 11.50 | 11.50 |
| Talc | 50.00 | 50 | 50 |
| Water |  |  | 681.83 |
| Total |  | 161.5 | 1076.66 |

Solid content of dispersion=15% w/w
Procedure:
1. Talc was homogenized in one third quantity of water for 20 min.
2. HPC LM was dissolved in remaining quantity of water for 30 min.
3. EUDRAGIT® NE30D and Talc dispersion were then mixed for 15 min.
4. Coating dispersion was filtered through 60# sieve and used for coating.
5. Coating was carried out using Pam Glatt 1.1 fluid bed processor.
6. Coating up to 10% of EUDRAGIT® NE 30D was done.
7. Pellets were cured for 24 hours at 50° C. in tray dryer.

Coating Parameters:

| Parameters | Unit | Value |
|---|---|---|
| Batch size | g | 400 |
| Nozzle | mm | 0.8 |
| Air flow | m³/h | 186-230 |
| Atomization pressure | bar | 1.0 |
| Spray rate | g/min | 1.0-10.0 |
| Inlet air temperature | ° C. | 30-35 |
| Product temperature | ° C. | 26-28 |

Example 15 (Inventive)

Bilayer Trial with EUDRAGIT NE 30D: Guar gum in 93:7 ratio
Core used: 10% EUDRAGIT® NE 30D (containing 11.5% HPC LM as pore former) coated
Metoprolol succinate pellets
Batch size: 80 g
Formulation Details:
Formula for 30% EUDRAGIT® NE 30D coating on 80 g pellets

|  | Ratio | % on polymer | Solids (g) | Quantity (g) |
|---|---|---|---|---|
| EUDRAGIT ® NE 30 D | 93 |  | 24 | 79.99 |
| Guar Gum medium viscosity 2000 cps | 7 | 7.53 | 1.81 | 1.81 |
| Talc |  | 100.00 | 24 | 24 |
| HPC LM |  | 22.00 | 5.28 | 5.28 |
| Methyl paraben |  | 0.18 | 0.0032 | 0.0032 |
| Propyl paraben |  | 0.09 | 0.0016 | 0.0016 |
| Yellow Iron Oxide |  | 0.50 | 0.12 | 0.12 |
| Water |  |  |  | 440.90 |
| Total |  |  | 55.21 | 552.11 |

Solid content of dispersion=1% w/w
Procedure:
1. Talc and yellow iron oxide was homogenized in water for 20 min.
2. Methyl paraben, HPC LM and Guar gum was dissolved in water under overhead stirring for 30 min.
3. Propyl paraben was dissolved in small quantity of hot water (50° C.) and then added to guar gum dispersion.
4. EUDRAGIT® NE30D and Talc dispersion were then added to the Guar gum solution and mixed for 15 min.
5. Coating dispersion was filtered through 60# sieve and used for coating.
6. Coating was carried out using Glatt 1.1 fluid bed processor.
7. Coating up to 30% of EUDRAGIT® NE 30D was done.
8. Pellets were cured for 24 hours at 50° C. in tray dryer.

Coating Parameters:

| Parameters | Unit | Value |
|---|---|---|
| Batch size | g | 400 |
| Nozzle | mm | 0.8 |
| Air flow | m³/h | 150-190 |
| Atomization pressure | bar | 1.0-1.2 |

-continued

| Parameters | Unit | Value |
|---|---|---|
| Spray rate | g/min | 2-5 |
| Inlet air temperature | ° C. | 29-34 |
| Product temperature | ° C. | 27-30 |

Results and Discussion of 14C & 15:

| Media | Time (min.) | 14C 0.1N HCl - buffer pH 6.8 % Release | 14C 40% Alco. 0.1N HCl - buffer 6.8 % Release | Deviation in Absolute % (14C) | 15 0.1N HCl - buffer pH 6.8 % Release | 15 40% Alco. 0.1N HCl - buffer 6.8 % Release | Deviation in Absolute % (15) |
|---|---|---|---|---|---|---|---|
| Acid stage | 0 | 0.0 | 0.0 | 0.0 | 0.0 | 0.0 | 0.0 |
| | 15 | 0.3 | 2.2 | +1.9 | 0.2 | 0.1 | −0.1 |
| | 30 | 0.3 | 15.0 | +14.7 | 0.0 | 0.0 | 0.0 |
| | 60 | 0.8 | 46.7 | +45.9 | 0.0 | 0.2 | +0.2 |
| | 90 | 1.8 | 68.9 | +67.1 | 0.2 | 1.6 | +1.4 |
| | 120 | 3.7 | 81.0 | +77.3 | 0.2 | 7.7 | +7.5 |
| Buffer stage | 240 | 30.5 | 98.3 | +67.8 | 18.1 | 26.0 | +7.9 |
| | 480 | 87.9 | 102.0 | +14.1 | 50.6 | 56.1 | +5.5 |
| | 720 | 101.1 | 102.9 | +1.8 | 93.1 | 76.9 | −16.1 |

Example 14C: Release profile in Ethanolic medium is higher than non-Ethanolic medium. This release profile appears/considered to be not following either Definition 1 ("plus or minus 20% definition") or definition 2 (Lower active ingredient release in media with ethanol"). Thus, Example 14C failed to give alcohol resistance.

Example 15: The release profile in the Ethanolic medium is as per Definition 1 ("plus or minus 20% definition"). Thus, composition of Example 15 is considered to be Ethanol resistant because of matching with Definition 1.

Example 16 C (Comparative example)

Trial with EUDRAGIT®RS30D: Guar gum in 93:7 ratio
Core used: Metoprolol pellets (16/20#)
Batch size:80 g
Formulation Details:
Formula for 40% EUDRAGIT® RS 30D coating on 80 g pellets

| | Ratio | % on polymer | Solid (g) | Quantity (g) |
|---|---|---|---|---|
| EUDRAGIT® RS 30 D | 93 | | 32 | 106.66 |
| Guar Gum High Viscosity (4219 cps) | 7 | 7.53 | 2.41 | 2.41 |
| TEC | | 15.00 | 4.80 | 4.80 |
| Talc | | 50.00 | 16 | 16 |
| Methyl paraben | | 0.18 | 0.004 | 0.004 |
| Propyl paraben | | 0.09 | 0.002 | 0.002 |
| Yellow Iron Oxide | | 0.50 | 0.16 | 0.16 |
| Water | | | | 792.8 |
| Total | | | 55.37 | 922.91 |

Solid content of dispersion=6% w/w

Procedure:
1. EUDRAGIT RS 30D and TEC were mixed together under overhead stirring for 15 min.
2. Talc and yellow iron oxide was homogenized in water for 20 min.
3. Methyl paraben and Guar gum was dissolved in water under overhead stirring for 30 min.
4. Propyl paraben was dissolved in small quantity of hot water (50° C.) and then added to guar gum dispersion.
5. EUDRAGIT RS30D and Talc dispersion were then added to the Guar gum solution and mixed for 15 min.
6. Coating dispersion was filtered through 60# sieve and used for coating.
7. Coating was carried out using Mycrolab Huttlin fluid bed processor.
8. Coating up to 40% of RS30D was done.

Coating Parameters:

| Parameters | Unit | Value |
|---|---|---|
| Batch size | g | 80 |
| Nozzle | mm | 0.6 |
| Air flow | m³/h | 23-25 |
| Atomization pressure | bar | 1.0 |
| Spray rate | g/min | 1.0-5.0 |
| Inlet air temperature | ° C. | 32-43 |
| Product temperature | ° C. | 27-28 |

Results and Discussion:

| Time (min.) | 0.1N HCl % Release | 40% Alcoholic 0.1N HCl % Release | Deviation in Absolute % |
|---|---|---|---|
| 0 | 0.0 | 0.0 | 0.0 |
| 15 | 0.0 | 5.0 | +0.5 |
| 30 | 0.0 | 49.3 | +49.3 |
| 60 | 1.7 | 93.1 | +91.4 |
| 90 | 43.0 | 99.2 | +56.2 |
| 120 | 73.4 | 99.9 | +26.5 |

Example 16C: Release profile in Ethanolic medium is higher than non-Ethanolic medium. This release profile appears/considered to be not following either Definition 1 ("plus or minus 20% definition") or definition 2 (Lower active ingredient release in media with ethanol"). Thus, Example 16C failed to give alcohol resistance.

The invention claimed is:
1. A pharmaceutical or nutraceutical composition, comprising:
 a) a core comprising a pharmaceutical or a nutraceutical active ingredient, and
 b) a coating layer comprising a mixture of 80 to 96% by weight of a water-insoluble (meth)acrylate polymer and 4 to 20% by weight of guar gum,- wherein the water-insoluble (meth)acrylate polymer comprises polymerized units of (i) more than 95 and up to 100% by weight of $C_1$- to $C_4$-alkyl esters of acrylic acid or $C_1$- to $C_4$-alkyl esters of methacrylic acid, and (ii) less than 5% by weight of acrylic acid or methacrylic acid;

wherein a 1% aqueous solution of the guar gum present in coating layer b) has a viscosity at 25° C. such that the release of the pharmaceutical or nutraceutical active ingredient from the pharmaceutical or nutraceutical composition under in-vitro conditions in a pH 1.2 medium according to USP with the addition of 40% (v/v) ethanol for 2 hours and subsequent buffer pH 6.8 medium according to USP is not more than plus or minus 20% (absolute percentage) of the release of the pharmaceutical or nutraceutical active ingredient from the same pharmaceutical or nutraceutical compositions in the same media under the same in-vitro conditions without the addition of ethanol in the pH 1.2 medium wherein a 1% aqueous solution of said guar gum w/w at 25° C. has a viscosity of 100 to 5,000 cp.

2. The pharmaceutical or nutraceutical composition according to claim 1, wherein the water-insoluble (meth)acrylate polymer is a copolymer comprising free-radical polymerized units of of 10 to 50% by weight ethyl acrylate and 50-90% by weight methyl methacrylate.

3. The pharmaceutical or nutraceutical composition according to claim 1, wherein the coating layer b) comprises 20 to 100% by weight of the mixture of the water-insoluble (meth)acrylate polymer and the guar gum and 0 to 80% by weight of pharmaceutical or nutraceutically acceptable excipients.

4. The pharmaceutical or nutraceutical composition according to claim 3, wherein the pharmaceutical or nutraceutically acceptable excipients are selected from the group consisting of antioxidants, preservatives, brighteners, binding Agents, flavouring Agents, flow aids, fragrances, glidants, penetration-promoting Agents, pigments, plasticizers, polymers different from the water-insoluble (meth)acrylate polymer and different from guar gum, pore-forming Agents, and stabilizers, or combinations thereof.

5. The pharmaceutical or nutraceutical composition, according to claim 1, wherein the release of the pharmaceutical or nutraceutical active ingredient in % under in-vitro conditions in a pH 1.2 medium according to USP with the addition of 40% (v/v) ethanol for 2 hours and subsequent buffer pH 6.8 medium according to USP does not differ by more than plus or minus 18.9% (absolute percentage) in the same media but without addition of ethanol in the pH 1.2 medium.

6. The pharmaceutical or nutraceutical composition, according to claim 1, wherein the release of the pharmaceutical or nutraceutical active ingredient in % under in-vitro conditions in a pH 1.2 medium according to USP with the addition of 40% (v/v) ethanol for 2 hours and subsequent buffer pH 6.8 medium according to USP is less than the release of the pharmaceutical or nutraceutical active ingredient in % under in-vitro conditions in a pH 1.2 medium according to USP in the same media but without addition of ethanol in the pH 1.2 medium.

7. The pharmaceutical or nutraceutical composition according to claim 1, wherein the release of the pharmaceutical or nutraceutical active ingredient under in-vitro conditions in a pH 1.2 medium according to USP for 2 hours and subsequent buffer pH 6.8 medium is 30 to 100% in a total time from 4 to 16 hours.

8. The pharmaceutical or nutraceutical composition according to claim 1, wherein the pharmaceutical or nutraceutical composition is in the form of a tablet, a pellet, a granule, a sachet or a capsule.

9. The pharmaceutical or nutraceutical composition according to claim 1, wherein, in addition to the coating layer b), the core a) comprises one or more polymer coating layers.

10. A process for producing the pharmaceutical or nutraceutical composition according to claim 1, said process comprising:
    forming the core a) comprising the pharmaceutical or a nutraceutical active ingredient by direct compression, compression of dry, wet or sintered granules, extrusion and subsequent rounding off, wet or dry granulation, direct pelleting or binding powders onto active ingredient-free beads or neutral cores or active ingredient-containing particles and
    applying the coating layer b) in the form of aqueous dispersions or organic solutions in spray processes or by fluidized bed spray granulation.

11. The process according to claim 10, wherein one or more additional coating layers are applied on the core a) in the form of aqueous dispersions or organic solutions in spray processes or by fluidized bed spray granulation.

12. The pharmaceutical or nutraceutical composition according to claim 1, which is a sustained or extended release pharmaceutical or nutraceutical composition with resistance against the influence of ethanol.

13. The pharmaceutical or nutraceutical composition according to claim 1, wherein the coating layer b) comprises a mixture of 90 to 96% by weight of a water-insoluble (meth)acrylate polymer and 4 to 10% by weight of the guar gum.

14. A pharmaceutical or nutraceutical composition, comprising:
    a) a core comprising a pharmaceutical or a nutraceutical active ingredient, and
    b) a coating layer comprising a mixture of 80 to 96% by weight of a water-insoluble (meth)acrylate polymer and 4 to 20% by weight of guar gum,
    wherein the water-insoluble (meth)acrylate polymer comprises polymerized units of (i) more than 95 and up to 100% by weight of $C_1$- to $C_4$-alkyl esters of acrylic acid or $C_1$- to $C_4$-alkyl esters of methacrylic acid, and (ii) less than 5% by weight of acrylic acid or methacrylic acid;
    wherein a 1% aqueous solution of the guar gum present in coating layer b) has a viscosity at 25° C. has a viscosity of 100 to 5,000 cp such that the release of pharmaceutical or nutraceutical active ingredient from the pharmaceutical or nutraceutical composition under in-vitro conditions in a pH 1.2 medium according to USP with the addition of 40% (v/v) ethanol for 2 hours and subsequent buffer pH 6.8 medium according to USP is less than the release of the pharmaceutical or nutraceutical active ingredient from the same pharmaceutical or nutraceutical composition in the same media under the same in-vitro conditions without the addition of ethanol in the pH 1.2 medium.

15. The pharmaceutical or nutraceutical composition according to claim 14, wherein the coating layer b) comprises a mixture of 90 to 96% by weight of a water-insoluble (meth)acrylate polymer and 4 to 10% by weight of guar gum.

16. The pharmaceutical or nutraceutical composition according to claim 1, wherein the coating layer b) comprises 5 to 30% by weight in relation to the water-insoluble polymer of a pore former excipient.

17. The pharmaceutical or nutraceutical composition according to claim 14, wherein the coating layer b) comprises 5 to 30% by weight in relation to the water-insoluble polymer of a pore former excipient.

18. The pharmaceutical or nutraceutical composition according to claim 1, wherein the coating layer b) contains less than 2% of neutral water-soluble celluloses.

19. The pharmaceutical or nutraceutical composition according to claim 14, wherein the coating layer b) contains less than 2% of neutral water-soluble celluloses.

* * * * *